(12) United States Patent
Kusleika et al.

(10) Patent No.: US 8,057,530 B2
(45) Date of Patent: Nov. 15, 2011

(54) MEDICAL DEVICES WITH AMORPHOUS METALS, AND METHODS THEREFOR

(75) Inventors: Richard S. Kusleika, Eden Prairie, MN (US); Rick Kravik, Champlin, MN (US)

(73) Assignee: Tyco Healthcare Group LP, Mansfield, MA (US)

( * ) Notice: Subject to any disclaimer, the term of this patent is extended or adjusted under 35 U.S.C. 154(b) by 370 days.

(21) Appl. No.: 11/771,890

(22) Filed: Jun. 29, 2007

(65) Prior Publication Data

US 2008/0125848 A1     May 29, 2008

Related U.S. Application Data

(60) Provisional application No. 60/818,162, filed on Jun. 30, 2006.

(51) Int. Cl.
*A61F 2/06* (2006.01)
(52) U.S. Cl. ...................................................... 623/1.15
(58) Field of Classification Search ........ 623/1.11–1.15; 148/421, 561
See application file for complete search history.

(56) References Cited

U.S. PATENT DOCUMENTS

| | | | |
|---|---|---|---|
| 3,856,513 A | 12/1974 | Chen et al. | |
| RE32,925 E | 5/1989 | Chen et al. | |
| 5,288,344 A | 2/1994 | Peker et al. | |
| 5,368,659 A | 11/1994 | Peker et al. | |
| 5,618,359 A | 4/1997 | Lin et al. | |
| 5,711,363 A | 1/1998 | Scruggs et al. | |
| 5,735,975 A | 4/1998 | Lin et al. | |
| 6,749,698 B2 | 6/2004 | Shimizu et al. | |
| 7,017,645 B2 | 3/2006 | Johnson et al. | |
| 7,335,426 B2* | 2/2008 | Marton et al. | 428/544 |
| 7,500,987 B2* | 3/2009 | Bassler et al. | 623/1.15 |
| 2002/0036034 A1* | 3/2002 | Xing et al. | 148/561 |
| 2002/0162605 A1 | 11/2002 | Horton et al. | |
| 2003/0111142 A1 | 6/2003 | Horton et al. | |
| 2004/0154702 A1 | 8/2004 | Shimizu et al. | |
| 2004/0267349 A1 | 12/2004 | Richter | |
| 2006/0076089 A1 | 4/2006 | Chang et al. | |
| 2006/0122687 A1 | 6/2006 | Bassler et al. | |
| 2006/0149391 A1* | 7/2006 | Opie et al. | 623/23.55 |

FOREIGN PATENT DOCUMENTS

| | | |
|---|---|---|
| EP | 1 036 612 B1 | 9/2000 |
| EP | 1 036 854 B1 | 9/2000 |
| EP | 1 308 527 A1 | 5/2003 |
| EP | 1 632 584 A1 | 3/2006 |
| WO | WO 03/064076 A1 | 8/2003 |
| WO | WO 2004/016197 A1 | 2/2004 |
| WO | WO 2004/045454 A2 | 6/2004 |

(Continued)

OTHER PUBLICATIONS

PCT Invitation to Pay Additional Fees in PCT/US2007/072594 dated November 12, 2008.

(Continued)

*Primary Examiner* — Suzette J Gherbi
(74) *Attorney, Agent, or Firm* — Elizabeth A. O'Brien, Esq

(57) ABSTRACT

Medical devices made at least in part of amorphous metals or alloys are provided. Certain embodiments include filters, stents, guidewires, snares, and coils comprised of amorphous metal. Methods of forming the medical devices, including methods of shape setting amorphous metals or alloys into components of medical devices are also provided. Methods of using amorphous metal medical devices are also provided.

76 Claims, 22 Drawing Sheets

FOREIGN PATENT DOCUMENTS

| | | |
|---|---|---|
| WO | WO 2006/026882 A1 | 3/2006 |
| WO | WO 2008/005898 A3 | 9/2009 |

OTHER PUBLICATIONS

U.S. Appl. No. 60/427,598, filed Nov. 18, 2002, Bassler et al.

Metallic Glass: Material of the Future, www.jhu.edu/~marsci/people/faculty/hufnagel/hufnagel.html (Mar. 30, 1998).

Liquidmetal Technologies; Various news and information bulletins; www.liquidmetal.com (2001-2002).

Schroers et al., "Amorphous Metal Alloys Form Like Plastic", Advanced Materials & Processes; 164(1):61-63 (Jan. 2006).

"Glassy Steel-ORNL researchers have developed a new bulk amorphous steel that is non-magnetic at room temperature and significantly harder than conventional steel", Oak Ridge National Laboratory, UT-Batelle LLC, Managed fro the US Department of Energy 175, 798, (Mar. 17, 2007).

PCT Notification Concerning Transmittal of International Preliminary Report on Patentability in PCT/US2007/072594 mailed Apr. 2, 2009.

Office Action for European Patent Application 07799 223.8, dated Mar. 23, 2010.

* cited by examiner

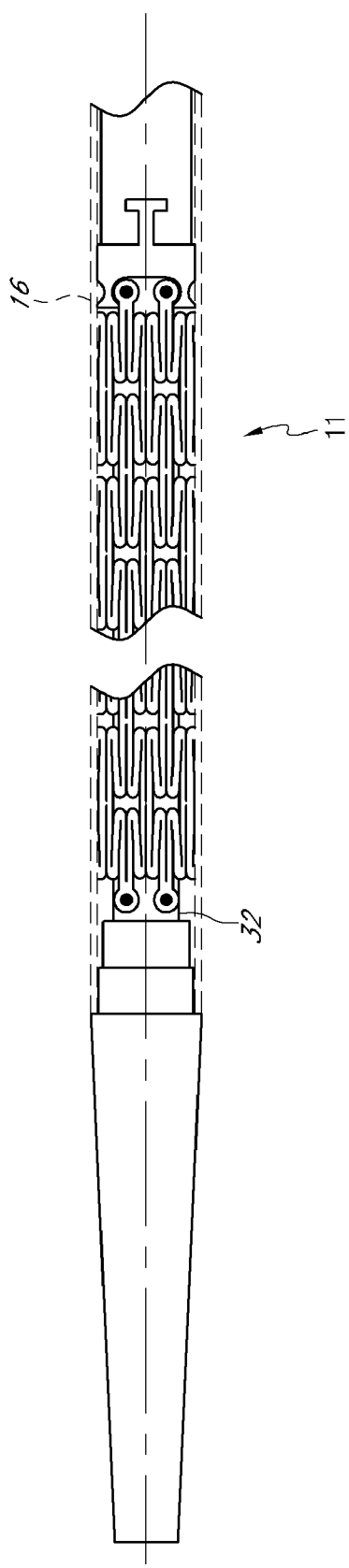
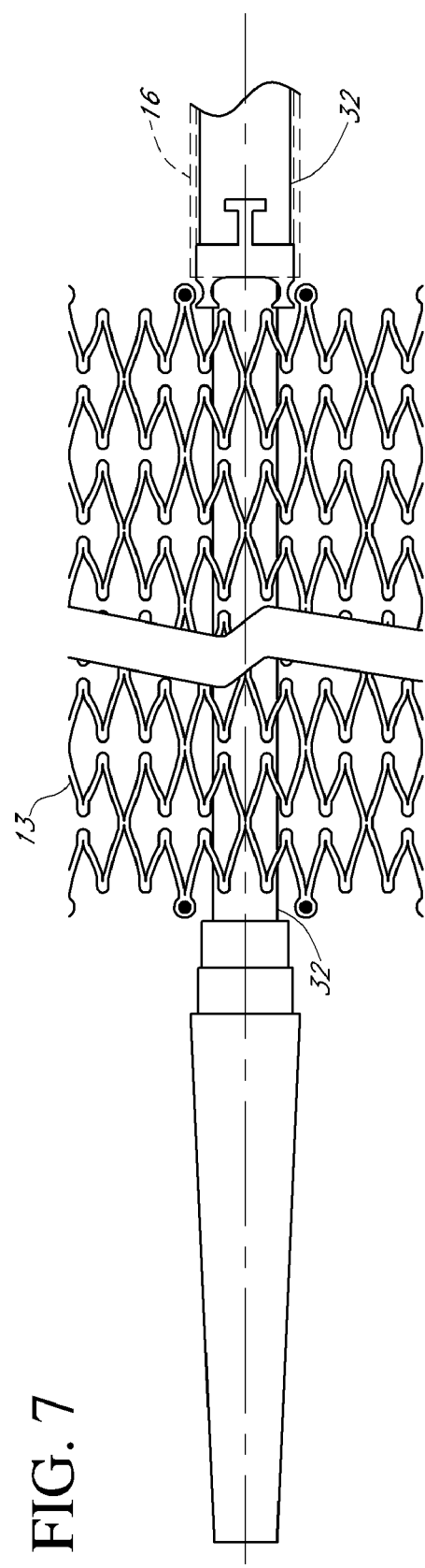
FIG. 6
FIG. 7

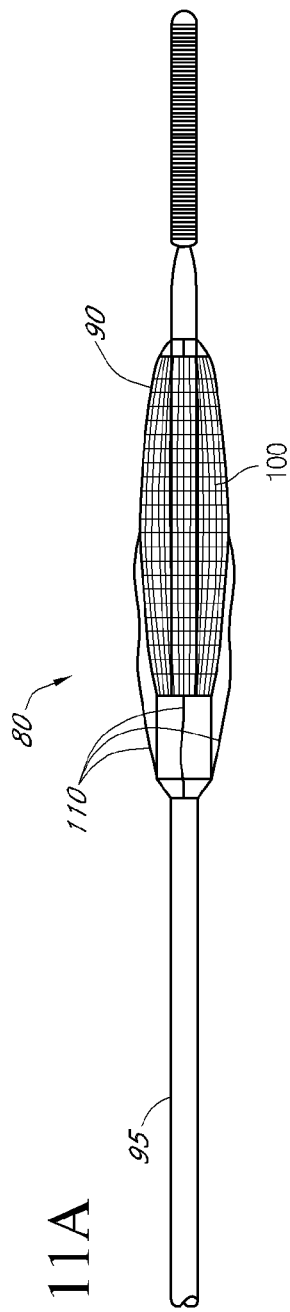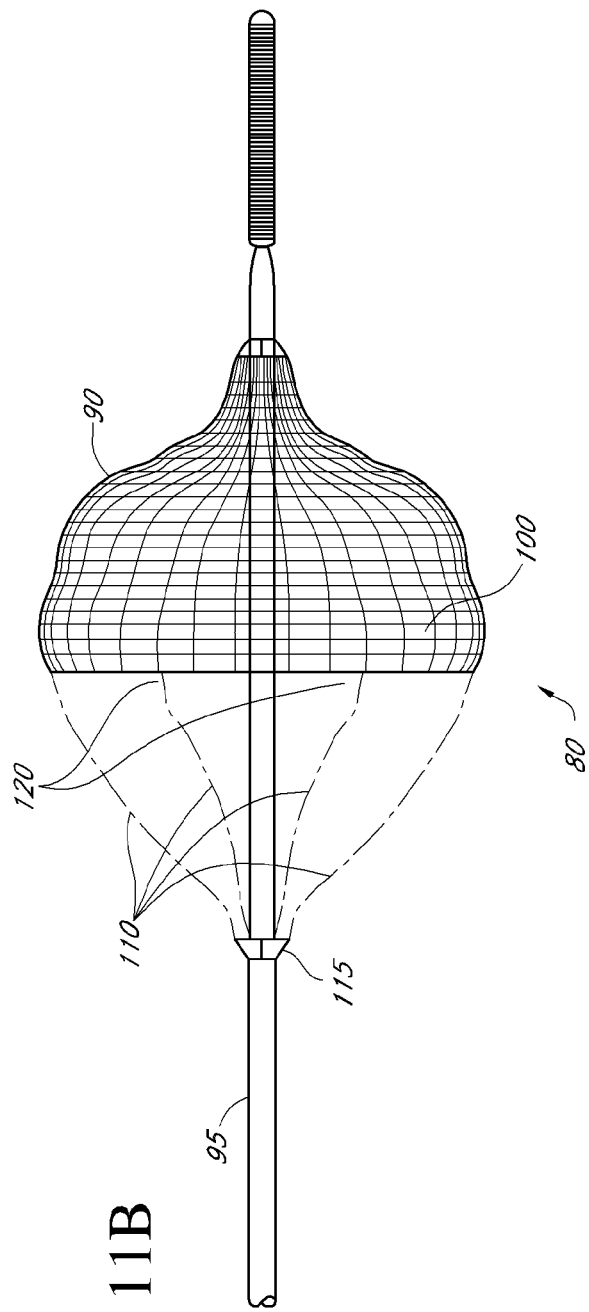
FIG. 11A
FIG. 11B

MEDICAL DEVICES WITH AMORPHOUS METALS, AND METHODS THEREFOR

CROSS-REFERENCE TO RELATED APPLICATIONS

This application claims the priority benefit under 35 U.S.C. §119(e) of the provisional application 60/818,162, filed Jun. 30, 2006, which is hereby incorporated by reference in its entirety.

BACKGROUND OF THE INVENTION

1. Field

This invention relates to medical devices, and, more particularly to internally deployed medical devices which can be used in naturally occurring or surgically created lumens, passageways, cavities, defects, holes, tissues, or other regions of the body. Such internally deployed devices include stents, embolic protection devices, guide wires, snares, catheters, neurovascular coils, septal defect closure devices, atrial appendage closure devices, staples, clips, etc. This invention also pertains to methods of manufacturing such medical devices and methods of using such medical devices.

2. Description of the Related Technology

The human body has many systems that include lumens in performing their function. The primary example is the vascular system, which transmits blood throughout the body through blood vessels having lumens. The body's breathing system, digestive system, reproductive system, nervous system and even skeletal system also have major or minor components comprised of lumens.

Almost since the beginning of surgery, surgeons have used the body's lumenal systems in medically treating the body. In some instances, the purpose of the surgery is to protect or repair the lumenal system itself. For instance, stents are commonly used to reinforce or hold open a blood vessel. In other instances, the surgical procedure uses the lumenal system to navigate through the body. In all instances in which surgical procedures are lumenally performed, the size of the lumen to some extent establishes the relative size of the medical devices being implanted or used during the surgery.

Internally deployed medical devices have been devised in a wide range of materials. Traditional metals such as stainless steel, originally used for a wide range of internally deployed medical devices, have been replaced in certain instances with other alloys, such as nitinol, ELGILOY, cobalt chrome alloys, tantalum, magnesium alloys, and other metals. In other instances, metal materials have been supplanted with polymeric, bio-polymeric, ceramic or bio-ceramic materials. These less traditional materials provide a variety of advantages. In some instances, materials such as nitinol are used due to their superelastic characteristics, and for their ability to be shape-set to a predetermined shape. Internally deployed implants can be bioabsorbable in whole or in part, or can release drugs or other active agents over time. Generally speaking, designers of internally deployed medical devices design new devices by considering materials which have already been used and approved in existing internally deployed devices. While internally deployed medical devices have greatly improved over the years, in part due to their improving designs and materials of construction, there is an ongoing opportunity for further improvement by using new materials and designs appropriate to the new materials.

Separate from the medical device field, many new materials are introduced to manufacturers. One type of such new material is amorphous metal or metal glasses. Amorphous metals are metals which have been transformed from an amorphous, molten state to a solid state at a speed or under conditions which prevent a crystalline atomic structure from evolving during the solidification process. Through work done at the California Institute of Technology ("Caltech"), the theoretical and actual physical existence of amorphous metals has been known since the 1960's. Still, actual implementation has been limited by the cooling speed necessary, which was only obtainable in samples having a thickness on the order of 100 microns or less. More recently, work done at Caltech and through companies such as Amorphous Technologies International (Laguna Niguel, Calif.) and Liquidmetal Technologies (Lake Forest, Calif.) has expanded the applicability of amorphous metals. For instance, U.S. Pat. Nos. 5,288,344 and 5,368,659, incorporated by reference, first disclose beryllium alloys which form metallic glass upon cooling below the glass transition temperature at a rate appreciably less than 1,000,000° C./sec. U.S. Pat. Nos. 5,618,359, 5,735,975 and 5,803,996, incorporated by reference, disclose alloys of titanium, zirconium and/or hafnium which form metallic glass upon cooling below the glass transition temperature at a rate appreciably less than 1,000° C./sec. U.S. Pat. Nos. 4,653,500, 5,976,274 and 6,325,868, incorporated by reference, disclose iron-based amorphous metal materials. U.S. Pat. No. 5,711,363, incorporated by reference, discloses alloys which form metallic glass upon cooling below the glass transition temperature at a rate appreciably less than 500° C./sec.

As there is currently a need to improve upon the medical devices formed from more traditional materials, it has been discovered that the physical properties of amorphous metal may be beneficial when used in internally deployed medical devices.

SUMMARY OF THE INVENTION

Described herein are medical devices. In some of the embodiments, internally deployed medical devices are described. In one embodiment, a medical device includes an amorphous metal. In some embodiments, the medical device is a shape set medical device. In some embodiments, the medical device is a filter, such as a braided filter, a stent, such as a self expanding or a balloon expandable stent, a stent delivery system, a guidewire, a snare, a coil, a catheter, a septal defect closure device, a left atrial appendage closure device, a staple, a clip.

In some embodiments, the medical device may include one or more amorphous metal filaments. Such filaments may have a diameter between about 0.010 inches (0.25 mm) about 0.00050 inches (0.013 mm).

In some embodiments, the medical device further comprises a coating on at least a portion of the amorphous metal. In some embodiments, the coating comprises one or more of a radiopaque coating, a drug coating, an active agent release coating, a biocompatible coating, or a lubricious coating.

In some embodiments, the amorphous metal medical device described herein have certain advantages when compared to more crystalline medical devices. For example, the medical device can be sufficiently corrosion resistant to be internally biocompatible. In some embodiments, medical device is capable of imaging under MRI.

In certain embodiments, the medical device includes amorphous and crystalline portions. In some embodiments, the medical device is capable of sustaining between about 0.5 volume percent to about 75 volume percent conversion of the amorphous metal into crystalline metal under storage or sterilization temperatures of less than 60° C. for a period of 2, 3, 4, or 5 years. In certain of these embodiments, less than about 1, 2, 5, 10, 15, 20, 25, 30, 40, 50, or 62 volume percent of the amorphous metal is converted to crystalline metal.

Methods of forming such amorphous metal medical devices are also described herein. In one embodiment, a method of forming a medical device or a component thereof includes shape setting a structure having an amorphous metal into the medical device or the component. In certain embodiments, the step of shape setting comprises heating a structure comprising an amorphous metal to an elevated temperature sufficient to shape-set the structure with the structure continuing to comprise an amorphous metal. In some embodiments, the step of shape setting includes providing the structure and expanding the structure into a first expanded structure on a mandrel. In certain embodiments, the step of shape setting may further include annealing at least a portion of the first expanded structure at a temperature about or above the glass transition temperature of the amorphous metal. In some embodiments, the step of annealing causes the first expanded structure to maintain the expanded shape. In some embodiments, the step of annealing is configured to convert at least a portion of the amorphous metal of the first expanded structure into crystalline metal. In some embodiments, the method may also include expanding at least some portion of the first expanded structure to form a second expanded structure. In these embodiments, method may also include annealing at least a portion of the second expanded structure at a temperature of about or above the glass transition temperature of the amorphous metal.

In certain embodiments, the step of shape setting includes expanding at least a portion of the structure and annealing the structure at about or above the glass transition temperature of the amorphous metal. In one embodiments, the glass transition temperature of the amorphous metal is greater than 140° F. (60° C.). In one embodiment, the glass transition temperature of the amorphous metal is greater than 160° F. (71° C.). In one embodiment, the glass transition temperature of the amorphous metal is greater than 180° F. (82° C.).

In certain embodiments, the step of shape setting includes converting at least a portion of the amorphous metal into a crystalline structure. In one embodiment, the method includes converting about 5 to about 75 volume percent of the amorphous metal to a crystalline metal. In another embodiments, the method includes converting about 10 to about 62 volume percent of the amorphous metal to a crystalline metal. In another embodiments, the method includes converting about 15 to about 40 volume percent of the amorphous metal to a crystalline metal.

In some embodiments of the medical devices and methods described herein, the structure is selected from the group consisting of a tube, a cylinder, one or more wires, one or more strands, and one or more ribbons.

In certain embodiments, a structure is shape set into a medical device or a component thereof. In some embodiments, the structure may be shape setting into a filter, such as braided filter or other filter element, a stent such as a self expanding or a balloon expandable stent, a stent delivery system or a portion thereof, a guidewire, a snare, a coil, a catheter, a septal defect closure device, a left atrial appendage closure device, a staple, or a clip.

Other embodiments include methods of using medical devices comprising amorphous metals. In some embodiments, a method of using a medical device includes inserting a shape set medical device comprising amorphous metal in a body lumen. In some embodiments, the method comprises delivering the shape set medical device into the body lumen in a collapsed configuration and expanding the shape set medical device in the body lumen. In any of these methods the shape set medical device is a filter, such as braided filter or other filter element, a stent such as a self expanding or a balloon expandable stent, a stent delivery system or a portion thereof, a guidewire, a snare, a coil, a catheter, a septal defect closure device, a left atrial appendage closure device, a staple, or a clip. In some embodiments, such methods may also include treating a treatment site with the shape set medical device. In some embodiments, the method also includes withdrawing the shape set medical device from the body lumen.

In some embodiment, a medical device includes a partially amorphous portion. In some embodiments, the portion includes a partially amorphous and partially crystalline metal. In any of these embodiments, the medical device is one or more of a filter, such as braided filter or other filter element, a stent such as a self expanding or a balloon expandable stent, a stent delivery system or a portion thereof, a guidewire, a snare, a coil, a catheter, a septal defect closure device, a left atrial appendage closure device, a staple, or a clip.

In one embodiment, a method of forming a partially amorphous and partially crystalline metal medical device includes providing a structure comprising an amorphous metal and converting the structure into a partially crystalline structure, wherein the partially crystalline structure is the medical device. In some embodiments, the method includes heating the structure in a manner sufficient to converting at least some of the amorphous metal to crystalline metal. In some embodiments, the method includes heating the structure to a temperature about or above the glass transition temperature of the amorphous metal.

Some embodiments include using the medical device a partially amorphous and partially crystalline metal medical device. In some embodiments, the method includes inserting the medical device into a body lumen. In some embodiments, the method includes delivering the medical device into the body lumen in a collapsed configuration and expanding the shape set medical device in the body lumen.

In some embodiments, a guidewire includes amorphous metal. In one embodiment, the guidewire is monofilament. In some embodiments, the monofilament includes amorphous metal. In another embodiment, the guidewire is multi-stranded, wherein one or more of a strand or filament of the multi-stranded guidewire comprises amorphous metal. Certain embodiments also include using such amorphous metal guidewires. In one embodiment, a method includes inserting the guidewire comprising amorphous metal in a body lumen.

In one embodiment, a stent delivery system comprising an amorphous metal structure is described. In some embodiments, the amorphous metal structure is a stylet or a reinforcing element. According to some embodiments, the stent delivery system is an over the wire system, a rapid exchange system, a fixed wire system. In some embodiments, the stent delivery system includes a self expanding or a balloon expandable stent, which may comprise amorphous metal. Certain embodiments also include methods of using the stent delivery system. In one embodiment, a method of using a stent delivery system comprising an amorphous metal include inserting a portion of the system in a patient, delivering a stent to a blood vessel, and expanding the stent to the walls of the blood vessel.

In one embodiment, a medical filter comprising amorphous metal is described. In some embodiments, the filter is an embolic protection filter. In some embodiments, a filter comprises a wire frame, at least a portion of the wire frame comprises an amorphous metal. In some embodiments, the filter comprises a filter element comprising amorphous metal filaments. In some embodiment, the filter element is braided.

In some embodiments, the filter has a pore size ranging from about 10 to about 1000 microns. In some embodiments, the filter has a pore size ranging from about 20 to about 500 microns. In some embodiments, the filter has a pore size ranging from about 30 to about 250 microns. In some embodiments, the filter has a pore size ranging from about 40 to about 150 microns. In some embodiments, the filter has a pore size ranging from about 50 to about 100 microns. In some embodiments, methods of using such amorphous metal filters are described. In one embodiment, a method of using the filter includes delivering the filter to a blood vessel.

In one embodiment, a snare comprising amorphous metal is described. In some embodiments, a method of using such snare includes delivering the snare to a blood vessel.

In one embodiment, a coil comprising amorphous metal is described. In some embodiments, a method of using such coil includes delivering the coil to a blood vessel.

In one embodiment, a catheter comprising amorphous metal is described. In some embodiments, a method of using such catheter includes inserting a portion of the catheter in a patient.

In one embodiment, a closure medical device includes amorphous metal. In some embodiments, the closure medical device is a septal defect closure device or a left atrial appendage closure device. A method of using such septal defect closure device includes delivering the septal defect closure device to a septal defect. A method of using such left atrial appendage closure device includes delivering the left atrial appendage closure device to a left atrial appendage.

In one embodiment, a medical staple comprising amorphous metal is described In another embodiment, a medical clip comprising amorphous metal is described.

In one embodiment, a medical device includes an at least partially amorphous metal surface. Such at least partially amorphous metal surface may have improved corrosion resistance when compared to a more crystalline metal surface. In certain embodiments, the medical device with improved corrosion resistance is selected from the group consisting of a filter, a catheter, a snare, a coil, a closure device, a medical staple, and a medical clip.

In one embodiment, a medical device includes a structure comprising amorphous metal. In some embodiments, the structure has one or more of improved MRI safety or improved MRI compatibility when compared to a more crystalline metal surface, wherein the medical device is selected from the group consisting of a filter, a catheter, a snare, a coil, a closure device, a medical staple, and a medical clip. In certain embodiments, the structure is capable of being MRI imaged.

In one embodiment, a method of forming a stent includes providing a foil of amorphous metal, forming the foil into a tube having a seam, and etching the tube to form a medical stent comprising a plurality of longitudinal segments. In certain embodiments, the step of providing the foil includes cooling a molten metal or alloy in a manner configured to produce a substantially amorphous metal foil. In some embodiments, the step of etching includes chemically etching the tube at a temperature lower than the glass transition temperature of the amorphous metal. In some embodiments, the step of etching includes chemically etching the tube in a manner configured to prevent the substantial crystallization of the amorphous metal. In some embodiments, such stent formed from the herein described methods have a wall thickness between about 0.00050 inches (0.013 mm) to about 005 inches (0.13 mm). In some embodiments, the stent has a wall thickness between about 0.00080 inches (0.013 mm) to about 0015 inches (0.13 mm).

In another embodiment, a method of forming a stent includes depositing a foil comprising amorphous metal around a substrate and removing at least part of the substrate from the foil to form a stent. In some embodiments, the step of depositing comprises vapor depositing the foil. In some embodiments, the step of removing comprises etching at least part of the substrate. In some embodiments, the step of removing comprises dissolving at least part of the substrate. In some embodiments, the step of removing is configured to prevent the substantial crystallization of the amorphous metal. In some embodiments, the substrate is substantially cylindrical. In some embodiments, the substrate is a stent skeleton.

In some embodiments, a method of forming a stent includes providing a tube comprising amorphous metal, cutting one or more openings in the tube to form a stent by a heat generating process. In some embodiments, the heat generating process is configured to substantially minimize crystallization of the amorphous metal. In some embodiments, the step of cutting comprises one or more heat generation processes selected from laser machining or electrostatic discharge machining. In some embodiments, the method may further include removing metal adjacent to the one or more openings by a cutting process. For example, the cutting process may be selected from one or more of chemical etching or microblasting at a temperature lower than the glass transition temperature of the amorphous metal.

In some embodiment, a medical device includes an amorphous metal structure, wherein the medical device is coated with one or more selected from the group consisting of a radiopaque coating, a drug coating, an active agent release coating, a biocompatible coating, or a lubricious coating. In some of these embodiments, the medical device is one or more selected from the group consisting of wherein the medical device is selected from the group consisting of a filter, a catheter, a snare, a coil, a closure device, a medical staple, and a medical clip.

In one embodiment, a method of forming an amorphous metal filter includes braiding one or more wire strands comprising an amorphous metal into a braided structure. In some embodiments, the method further includes molding the braided structure into a filter body. In some embodiments, the step of molding includes applying axial tension to the braided structure against a mandrel. In some embodiments, the mandrel may include a proximal projection for forming one or more proximal openings in the filter body. In some embodiments, the one or more wire strands project about the periphery of the projection. In some embodiments, the method may further include fixing the lengths of the one or more wire strands, thereby causing the filter body to retain a shape. In certain embodiments, the step of molding includes heating the filter body to a temperature of about or above the glass transition temperature of the amorphous metal. In some embodiments, the step of heating is configured to substantially prevent conversion of the amorphous metal to a crystalline metal. In some embodiments, the step of heating is configured to cause at least partial conversion of the amorphous metal to a crystalline metal. In some embodiments, the step of heating is configured to cause complete conversion of the amorphous metal to a crystalline metal.

All of these embodiments are intended to be within the scope of the invention herein disclosed. These and other embodiments of the present inventions will become readily apparent to those skilled in the art from the following detailed description of a preferred embodiments having reference to the attached figures, the invention not being limited to any particular preferred embodiment(s) disclosed.

BRIEF DESCRIPTION OF THE DRAWINGS

FIG. 6 is an enlarged view of the distal end of the system of FIG. 5.

FIG. 7 is a view of the distal end shown in FIG. 6 with the outer sheath retracted.

FIG. 11A is a schematic side view of an alternative filter in a collapsed state for delivery to an internal deployment site.

FIG. 11B is a schematic side view of the filter of FIG. 11A in an expanded state.

Figure 1:
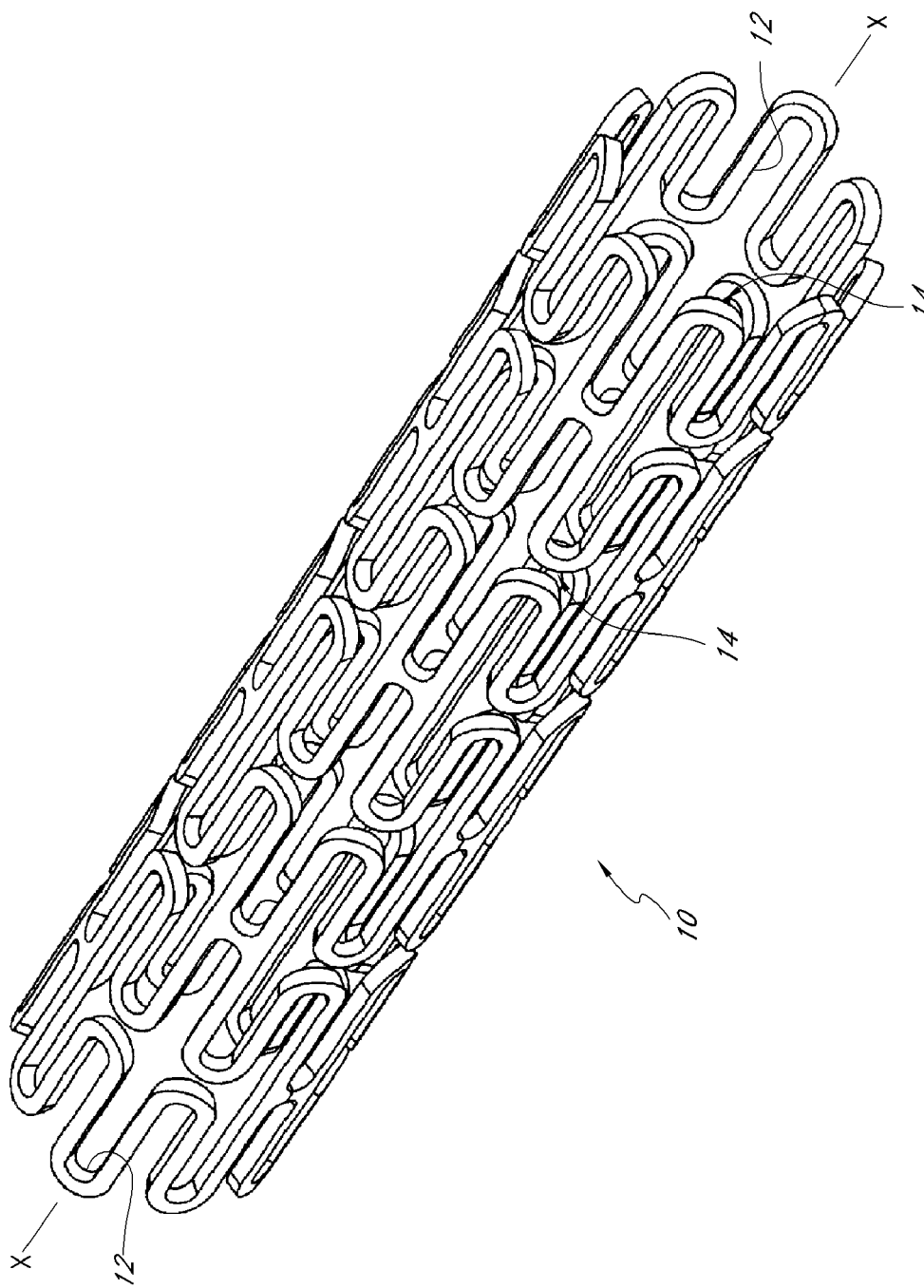
FIG. 1 is a perspective view of a stent.

While the above-identified drawing figures set forth preferred embodiments, other embodiments are also contemplated, some of which are noted in the discussion. In all cases, this disclosure presents the illustrated embodiments by way of representation and not limitation. Numerous other minor modifications and embodiments can be devised by those skilled in the art which fall within the scope and spirit of the principles of these inventions.

DETAILED DESCRIPTION OF THE PREFERRED EMBODIMENT

According to certain embodiments described herein, amorphous metal technology is applied in internally deployed medical devices. As used herein, "amorphous metal" is a broad term used in its ordinary sense and includes both amorphous metals and amorphous metal alloys. Embodiments described herein may include medical devices comprising amorphous metals. Such embodiments may include one or more of amorphous metals, amorphous metal alloys or combinations thereof. Internally deployed medical devices may be partially or completely formed of amorphous metal or may include components partially or completely formed of amorphous metal. Moreover, amorphous metal or amorphous metal medical devices are not limited to solely amorphous structures. In certain embodiments, a medical device may include a portion having both a crystalline and an amorphous metal structure. Such embodiments are further described herein.

For any solid metal or metal alloy comprised of crystalline structure, the physical and mechanical properties that are influenced by the presence of crystalline structure are likely to be altered in the same metal or metal alloy when it is solidified into an amorphous structure. With their different physical or mechanical properties, amorphous metals offer a variety of unique and superior characteristics that make them suitable for certain applications in internally deployed medical devices.

For example, it is not unusual for a metal alloy to be brittle when in crystalline form and ductile when in amorphous form. The crystalline form of certain alloys may also have a lower elastic yield limit than their amorphous counterparts. Generally, this is because the crystalline metal yields via a process involving dislocations (microscopic or sub-microscopic defects in the crystal lattice), but in an amorphous structure dislocations have no crystal lattice in which to operate and/or propagate.

Corrosion characteristics of amorphous metal alloys are often different than corrosion characteristics of the same alloy in crystalline form. This is because when crystalline alloys solidify, different phases can separate and different phases can have different galvanic potentials (a driving force for corrosion), while in an amorphous metal little or no such segregation occurs. Also, in crystalline metals, intragranular corrosion can occur at weak grain (crystal) boundaries. In amorphous metals, there are no grains and therefore intragranular corrosion does not generally occur. In one embodiment, an amorphous metal can be selected for an internal medical device that provides sufficient corrosion resistance to be biocompatible and useable within a human body.

Magnetic properties of amorphous metal alloys are often different than magnetic properties of the same alloy in crystalline form. This is because magnetic domains are influenced by the presence of crystalline structure. A metal alloy in amorphous form, imaged under magnetic resonance imaging (MRI), may be more MRI Safe (less heating or movement in the magnetic field) or MRI Compatible (produce less artifact) than the same alloy in crystalline form due to the different magnetic properties of the amorphous alloy. Because of these and other physical or mechanical differences between crystalline and amorphous forms, alloys that are unsuitable for use in medical applications when in crystalline form may be suitable for use in such applications when in amorphous form. Thus, in one embodiment an internal medical device is provided that is capable of imaging under MRI.

Amorphous metals can be considered "metastable", meaning that if an amorphous metal is heated above a certain temperature (the exact temperature being dependent on the metal or alloy, but generally above the glass transition temperature $T_g$ of the amorphous metal or alloy as determined by differential scanning calorimetry) the atoms will rearrange themselves from an amorphous structure into a crystalline structure, and the enthalpy of crystallization will be released. When the amorphous metal converts into a crystalline structure, amorphous properties will be lost and crystalline properties will be gained. A metal or alloy can be partially converted from an amorphous to a crystalline structure by heating at an intermediate temperature. Generally, for a given temperature, the amount of conversion achieved will increase with the length of time the metal or alloy is held at that temperature, and the amount of conversion achieved in a given time will generally increase at higher temperatures.

Because of the metastable nature of amorphous metals, manufacture of internally deployed medical devices can require different processing techniques than those prior art techniques used with crystalline metals. In some embodiments, it is important to choose an amorphous metal that has no significant conversion to crystalline structure during the processing and storage conditions used for medical device manufacture, distribution, and use. For instance, the amorphous metal alloy should have no significant conversion to crystalline structure during joining, fabrication, finishing, sterilizing, shipping, storing, accelerated aging, using and other processes that internally deployed medical devices incur. It is contemplated that medical devices comprised of amorphous metals will be manufactured to sustain between 0.5 volume percent to 75 volume percent conversion of amorphous into crystalline structure under storage or sterilization temperatures of less than about 60° C. for periods of up to 2, 3, or 5 years. In various embodiments, less than 1, 2, 5, 10, 15, 20, 25, 30, 40, 50, or 62 volume percent of amorphous structure is converted into crystalline structure under these conditions.

Generally speaking, in one embodiment, to assure stable properties of a medical device comprised of amorphous metals, the amorphous metals should have a glass transition temperature $T_g$ higher than the processing, storage and use conditions listed above. In some embodiments, $T_g$ of the amorphous metal is greater than 140° F. (60° C.). In some embodiments, $T_g$ of the amorphous metal is greater than 160° F. (71° C.). In some embodiments, $T_g$ of the amorphous metal is greater than 180° F. (82° C.).

In other embodiments, because of the metastable nature of amorphous metals, it is possible to anneal or otherwise treat the amorphous form so as to convert a portion of the metal or alloy into crystalline form. A partially converted metal or alloy will have properties that are intermediate between those of the amorphous structure and those of the crystalline structure. Therefore, some properties of partially converted metals or alloys can be tailored to meet the needs of the medical device. For example, an alloy can be processed into partially or fully amorphous wire, foil or ribbon, converted in part to crystalline structure by annealing above $T_g$ for about 20% to about 80% of the time needed to 100% convert the alloy into crystalline form at that annealing temperature, and then the partly converted alloy is fabricated into a medical device such as a stent or a guidewire coil. It is contemplated that conversion of between 5 volume percent and 75 volume percent amorphous into crystalline structure is desirable. In various embodiments, 10, 15, 20, 25, 30, 40, 50, or 62 volume percent of amorphous structure is converted into crystalline structure.

In another embodiment, it is possible to anneal or otherwise treat the amorphous form so as to cause it to assume a preset shape. For example, an alloy can be processed into partly or fully amorphous wire, foil, ribbon or other forms, constrained by a mold, then annealed at a temperature near to or above $T_g$, causing the alloy to assume the shape of the mold. In some embodiments, the mold can have a cavity and can have mating parts to hold the alloy in a desired shape. In some embodiments, the mold can be a surface such as a plate, a mandrel, a tapered mandrel, or other surface and the alloy can be pressed against the surface or simply held in proximity to the surface using tension on the alloy (for example, stretched across the surface). In some embodiments, the mold can be plaster, resin, or other hardenable material interdigitated into the interstices of a mesh like part comprised of amorphous alloy.

Shape setting of amorphous alloys can be advantageous for applications in medical devices. A commonly used metal in medical devices which can be shape set is nitinol, in one variation a roughly equiatomic alloy of nickel and titanium. While nitinol alloys are widely used for medical devices, these alloys have certain limitations. They are hard to join to themselves and to other materials because application of heat can compromise the mechanical properties of nitinol. When welded (for example) to steels, brittle compounds can form which weaken the welds. It is well known that some individuals have nickel sensitivity. In some forms nitinol alloys can have high concentration of nickel on the surface. Also, corrosion of nitinol releases nickel into the body. Further, one is limited to the chemical, corrosive, magnetic, acoustic, mechanical, and other properties of nitinol alloys.

In contrast, amorphous alloys can be produced from a wide range of alloy compositions having more desirable mechanical, fabrication, joining, corrosive, biocompatibility, acoustic, magnetic, or other properties for the application at hand and can be shape set into forms useful as medical devices. These medical devices and methods of forming the medical devices, including methods that are not limited to shape setting, are further described herein.

I. Amorphous Metal Medical Devices

A. Stents

Amorphous metals can be used in internally deployed medical devices such as stents. In some embodiments, amorphous metal may be used in stent designs which have previously used crystalline metals such as stainless steel, cobalt chrome alloy or nitinol which formed the material of the stent, thereby replacing the crystalline material of the stent body with amorphous or partially amorphous metal. For example, FIGS. 1-3, adapted from U.S. Pat. No. 6,558,415 and incorporated by reference in its entirety ("'415 stent"), show two embodiments of a stent.

Figure 2:
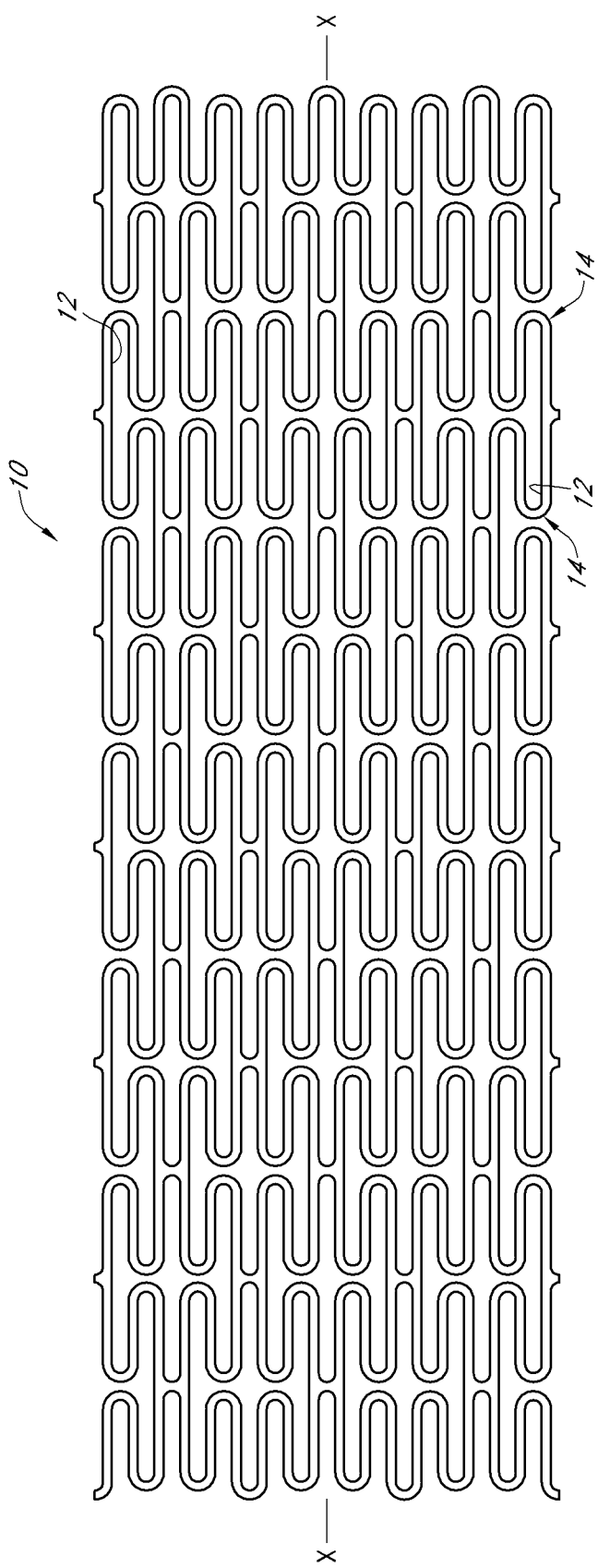
FIG. 2 is a plan view of the stent of FIG. 1 as it would appear if it were cut longitudinally and laid out flat.
Figure 3:
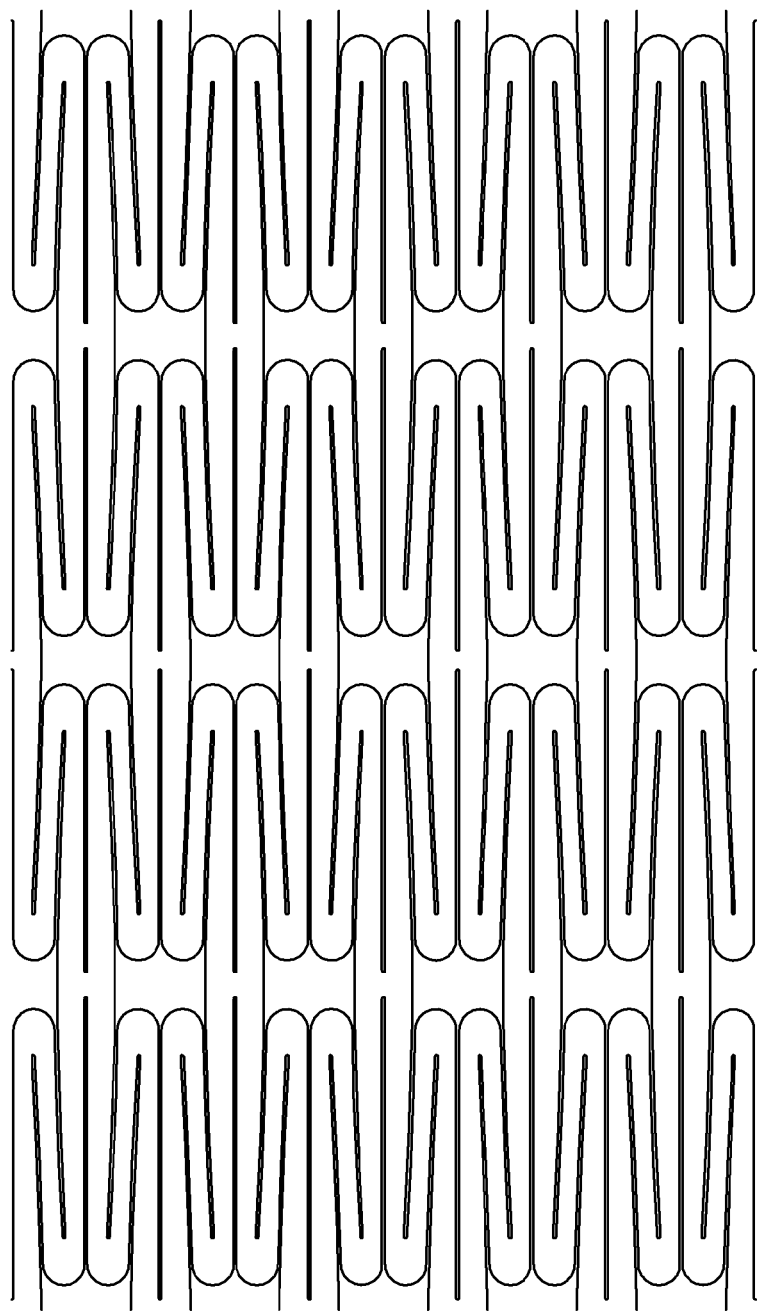
FIG. 3 is a plan view of an alternative stent as it would appear if it were cut longitudinally and laid out flat.

Referring to FIG. 1-3, the stent has a stent body 10 generally defining a cylindrical tube about a longitudinal axis X-X. The stent body 10 is made up of a plurality of cells 12, each cell 12 having two or more longitudinal segments 14 joined so the overall stent body 10 can change its diameter from an un-deployed condition to a radially expanded deployed condition. In some embodiments, the stent can either be balloon expandable or self-expanding. In some embodiments, it is desirable for the stent to be flexible along its longitudinal axis X-X to permit the stent to be advanced through arcuate or tortuous paths to a deployment site. When deployed, the stent can support a radially-directed compressive force, pushing a wall of a blood vessel or other opening in the patient's body outward. For example, stents may be used to maintain patency of a coronary artery, carotid artery, cerebral artery, or other blood vessels including veins, or other body lumens such as the ureter, urethra, bronchus, esophagus, or other passages.

The '415 stent was formed of stainless steel or nitinol, or other known materials such as MP35N, tantalum, platinum, gold, ELGILOY and PHYNOX, whereas the stent of FIGS. 1-3 is formed of an amorphous metal. Being formed of an amorphous metal, the stent avoids the crystalline defects present when the '415 stent is formed. Such crystalline defects lead to a reduced relative tensile strength of the '415 stent for the desired resiliency and size of the stent. The '415 stent had an exemplary size of longitudinal segments 14 of about 0.0065 inch (about 0.16 mm) in width and about 0.0057 inch (about 0.14 mm) in thickness. Stainless steels and nitinol have yield strengths on the order of 200-600 MPa leading to the desired dimensions. In contrast, amorphous metals can have yield strengths on the order of about 1.5 to about 3 GPa or more.

In one embodiment, the amorphous metal material of the stent enables the stent to be formed with a smaller stent body diameter than the '415 stent and thereby treat vessels or openings of smaller diameter. For example, the longitudinal segments 14 may be about 0.0032 inch (about 0.08 mm) in width and about 0.0028 inch (about 0.07 mm) in thickness, and the stent body may have an un-expanded diameter of 0.040 inches. Another embodiment provides a stent of the same un-expanded and expanded nominal diameters as the '415 stent, with an exemplary longitudinal segment size of about 0.0065 inch (about 0.16 mm) in width. However, rather than use material of about 0.0057 inch (about 0.14 mm) in thickness as is described with the '415 stent, certain embodiments of amorphous stents described herein enable a decrease in the material thickness in accordance with the increase in yield strength, to a material on the order of 0.0010 inch in thickness. This change of dimension in wall thickness of the stent, not in longitudinal segment width, allows the stent to present the same metal surface area to the vessel wall as the prior art '415 stent. With the large decrease in wall thickness but same external surface area, the stent has a superior lesion crossing profile. The decrease in wall thickness also provides increased flexibility for the stent for improved deliverability through tortuous anatomy, allowing the stent to be delivered to the deployment site with lower advancement forces. At the same time, the decrease in thickness of the material creates a much larger surface area for given cross-section of the longitudinal segments, allowing the material to release heat much more quickly during manufacture and thereby avoiding crystallization of metal grains.

In some embodiments, the amorphous metal composition of the stent provides a higher elastic yield limit than other known stent materials of the same crystalline compositions. In some embodiments, the amorphous metal composition of the stent also provides better corrosion resistance for the same crystalline alloy compositions. In some embodiments, the amorphous metal composition of the stent provides higher fatigue life for the same crystalline alloy compositions as are presently used. Both better corrosion resistance and higher fatigue life are very important factors for permanent implants such as stents which can be implanted for decades. According to one embodiment, an amorphous metal stent has one or more of the improved properties described above.

Figure 4:
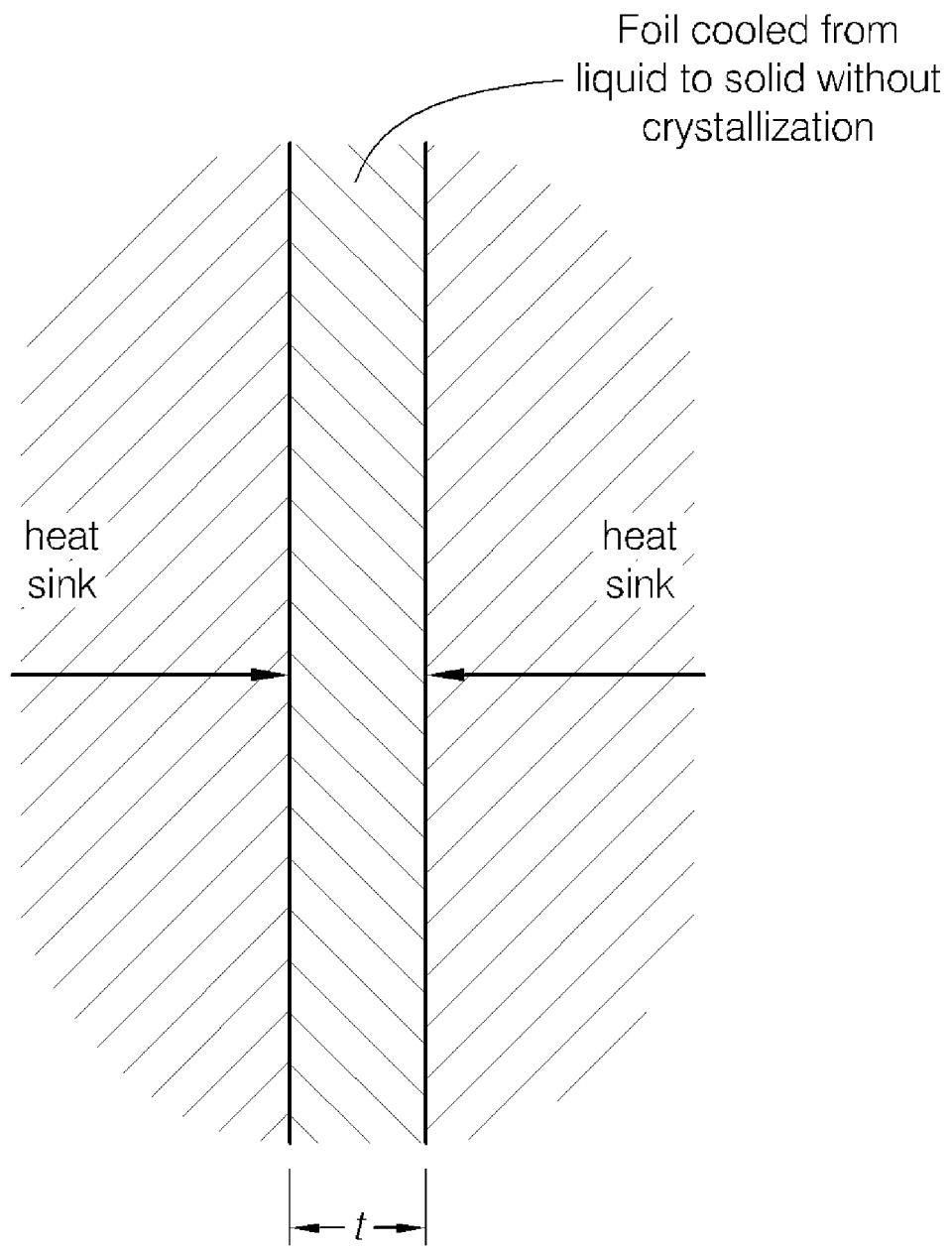
FIG. 4 is a cross-sectional view of a preferred forming method for foil used to create the stent of FIGS. 1-3.

In some embodiments, a method of forming the amorphous metal stent includes forming a foil of amorphous metal by rapidly cooling molten metal or alloy between two planar, refrigerated heat sinks as shown in FIG. 4. Such foils may be formed having various thicknesses. In some embodiments, the final wall thickness t of the stent is about 0.0010 inches (0.025 mm). In some embodiments, the final wall thickness t of the stent is between about 0.00050 inches (0.013 mm) to about 0.0050 inches (0.13 mm). In other embodiments, the final wall thickness t of the stent is about 0.00080 inches (0.020 mm) to about 0.0015 inches (0.038 mm). If desired in some embodiments, the heat sinks may be moved toward each other during the cooling process, thereby spreading the molten metal into the foil immediately prior to solidification. In some embodiments, the foil is formed into a tube with a seam, with the seam formed by bonding, riveting, mechanical interlock, or other means that do not involve heating the foil. In other embodiments, the seam could also be formed by soldering, brazing or welding, providing such joining processes are subject to temperature controls and are accomplished without significant crystallization of the amorphous metal material. After the seam is formed, the stent may be chemically etched to form the longitudinal segments. The chemical etching process may occur at low temperatures, generally lower than the $T_g$ of the metal, so as to avoid any generation of crystallization within the amorphous metal material of the stent.

A second preferred method of forming the stent includes vapor depositing a foil of amorphous metal about a cylindrical substrate, and then etching, dissolving or otherwise removing the cylindrical substrate from the cylindrical foil. In some embodiments, the cylindrical foil of amorphous metal is then chemically etched through the cylindrical sidewall into a profile. Again, the chemical etching process may occur at low temperatures to prevent the substantial inducement of grain formation.

In some embodiments, a third method of forming an amorphous metal stent includes forming a stent skeleton. The stent skeleton may be formed of various materials, including crystalline metal or alloys. In one embodiment, the stent skeleton is formed of stainless steel. Thereafter, amorphous metal may be vapor deposited about the stent skeleton. Advantageously, the longitudinal segments of the stent skeleton can be made extremely thin, because the majority of the compressive loads borne by the stent are supported by the amorphous metal outer layer rather than by the stent skeleton. Other materials, including brittle materials, can be used for the stent skeleton, particularly if such stent skeletal materials inhibit grain formation of the amorphous metal during vapor deposition.

A fourth method of forming an amorphous metal stent is through a molding/deposition technique similar to that disclosed in U.S. Pat. No. 6,203,732, which is incorporated by reference in its entirety. The metal alloy can be deposited onto the mold in an amorphous form using processes such as vapor deposition, by spraying liquid metal droplets onto the mold surface, or other methods. Again, care may be taken during forming to avoid crystal growth during solidification of the amorphous metal into the depressed pattern in the external surface of the mold and during the process of removing excess material from the mold.

A fifth method of forming an amorphous metal stent includes forming an amorphous metal tube and then using a heat generating process, such as the laser machining taught in U.S. Pat. No. 6,558,415 (using, for instance, a laser cutter as marketed by Lasag Industrial-Lasers USA of Buffalo Grove, Ill.) or the electrostatic discharge machining (EDM) taught in U.S. Pat. No. 6,107,004, both incorporated by reference, but modifying the process in a way that reduces temperature buildup in the amorphous metal material. For instance, in the laser machining process, the laser can be pulsed, allowing the material to self-quench during the "no power" portion of the series of pulses. Alternatively or in addition to pulsing of the laser, the stent can be chilled before and during the heat generating process, such as chilling the stent before and/or during the laser cutting procedure. Both methods are intended to minimize the extent of crystallization caused through heat generation processes. In some embodiments, the openings cut by laser machining or by EDM should be smaller than the desired final openings of the stent profiles shown in FIGS. 1-3. Due to the heat generated in some of these methods, neighboring metal to the openings formed in the heat-generating process may crystallize. Thus, the manufacture of the amorphous metal stent structure may involve chemical etching, microblasting, or another low temperature process to remove metal adjacent the openings made by the heated cutting process, thereby assuring that crystallization formed during the heating process is removed by the low temperature process.

In yet another embodiment, a brittle metal alloy can be processed into an amorphous structure. Such brittle alloy may be fabricated while ductile. According to some embodiments, the brittle alloy is shaped as desired. The step of shaping may include one or more of constraining, expanding, bending, flexing, or two or more of the aforementioned. According to some embodiments, the shaped metal alloy may then be annealed to convert the alloy at least partially into a crystalline structure, thereby substantially retaining the constrained shape. For example, after cutting openings through the wall of an amorphous metal tube, the tube can be expanded onto a mandrel and subsequently annealed at a temperature near to or above $T_g$, thereby causing the expanded stent to assume the expanded shape and optionally converting the structure to at least a partially crystalline structure. In another embodiment, the stent is expanded onto a mandrel and subsequently annealed at a temperature near to or above $T_g$ of the metal or metal alloy to cause the expanded stent to partially convert to crystalline structure and assume the expanded shape. Thereafter, the expanded stent may be further expanded onto an even larger mandrel and further annealed at a temperature near to or above $T_g$, thereby causing the expanded stent to more fully convert to crystalline structure and to remember the shape of the larger mandrel. In some embodiments, a portion of the expanded stent is further expanded on a larger mandrel, thus allowing for selective expansion of the medical device.

With all of these embodiments, depending upon the properties desired for the final stent, the amorphous metal can be annealed or laser heated (possibly followed by quenching), aged or otherwise treated so as to convert a portion of the amorphous metal or metal alloy into a partially or fully crystalline form. According to some embodiments and as suggested above, a partially converted metal or alloy may have the properties that are intermediate between those of the amorphous structure and those of the crystalline structure.

Regardless of which method is used to create the stent, coatings may be placed over the amorphous metal material for various performance attributes. For instance, radiopaque coatings, or drug (such as an antibiotic, anticoagulant, antiproliferative, antirestenotic, or growth hormone) or other active agent release coatings, may be applied over the amorphous metal material of the stent. If the amorphous metal selected is non-biocompatible, a biocompatible coating may be applied over the non-biocompatible amorphous metal for use in the internally deployed medical device. Lubricity may be provided by a coating of a low friction polymer such as polyurethane, hydrogels, polyethylene, polytetrafluoroethylene (PTFE) and TEFLON, as taught in U.S. Pat. No. 6,107,004, incorporated by reference in its entirety.

While the amorphous metal stent embodiments have been described with reference to modifications to the '415 stent, the principles of these embodiments can be equally applied to other stent designs. Examples of such other stent designs are those sold by ev3 Incorporated (Plymouth, Minn.) under trade names PROTÉGÉ, EVERFLEX and INTRASTENT, and stent designs disclosed in other patents such as U.S. Pat. No. 6,814,746, incorporated by reference in its entirety. In some embodiments, amorphous metal can also be used in place of other stent materials, such as cobalt chromium alloys, magnesium alloys and bioabsorbable metals.

B. Stent Delivery Systems

In addition or alternatively to forming the stent body out of amorphous metal, amorphous metal can be used in a portion of a stent delivery system, such as a stylet or reinforcing element. Delivery systems suitable for self expanding stents comprised of amorphous metal can be over the wire systems, for example the system described in U.S. Pat. No. 6,814,746 (incorporated by reference herein), can be rapid exchange systems, for example the system described in U.S. Patent Application No. 60/680,400 (incorporated by reference herein), or can be fixed wire systems. Delivery systems suitable for balloon expandable stents comprised of amorphous metal can be over the wire systems, can be rapid exchange systems, or can be fixed wire systems, and typically comprise a deflated inflatable balloon with a stent compressed thereon.

Figure 5:
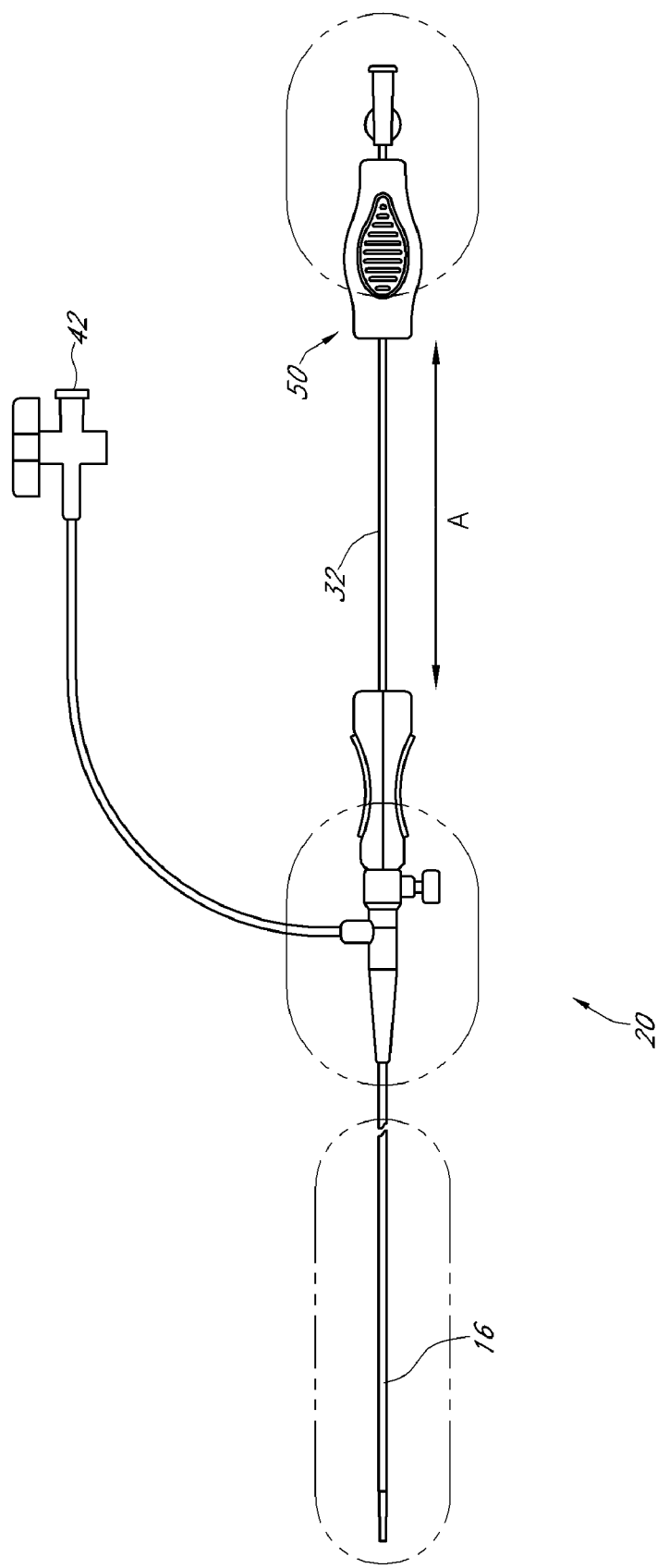
FIG. 5 is a side elevation view of a delivery system utilizing the stent.

As an example, FIGS. 5-7 show several examples of stent delivery systems for delivering a self expanding stent to a deployment site. Referring to FIG. 5, the stent delivery system 20 includes an inner member 32 coupled to one handle 50 and a retractable outer sheath 16 coupled to a second handle 42. As shown in FIG. 6, a stent 13 may be positioned around the inner member 32 near its distal end 11, and held inward in a compressed state by the outer sheath 16. As shown in FIG. 7, when the stent 13 has been advanced to the deployment site, relative movement between the handles 42, 50 retracts the outer sheath 16 from over the stent, and the stent releases from the delivery system and expands radially at the deployed location.

In some embodiments, a stent delivery system or a stent may additionally include a reinforcing element comprising amorphous metal. In some embodiments, a reinforcing element includes a braided material or, sometimes, a spirally wound material. As a nonlimiting example, braided amorphous metal reinforcement elements are particularly useful for providing axial strength to the exterior tube of a multi-lumen catheter because the multi-lumen catheter is particularly susceptible to kinking or ovalization of the circular cross-sections of the various lumens when the catheter is exposed to a high flexure or a high torsion, such as when the catheter is passed through the bends or turns of the vascular system.

In some embodiments, a stent delivery system includes a amorphous metal stylet or other holding element. Such amorphous holding element may to facilitate initial placement of stent within a body lumen. For example, a amorphous metal stylet may be used the anchor a stent beyond a constraining sheath where the anchor is allowed to expand into its preformed or radially expanded configuration.

C. Embolic Protection Devices

Figure 8:
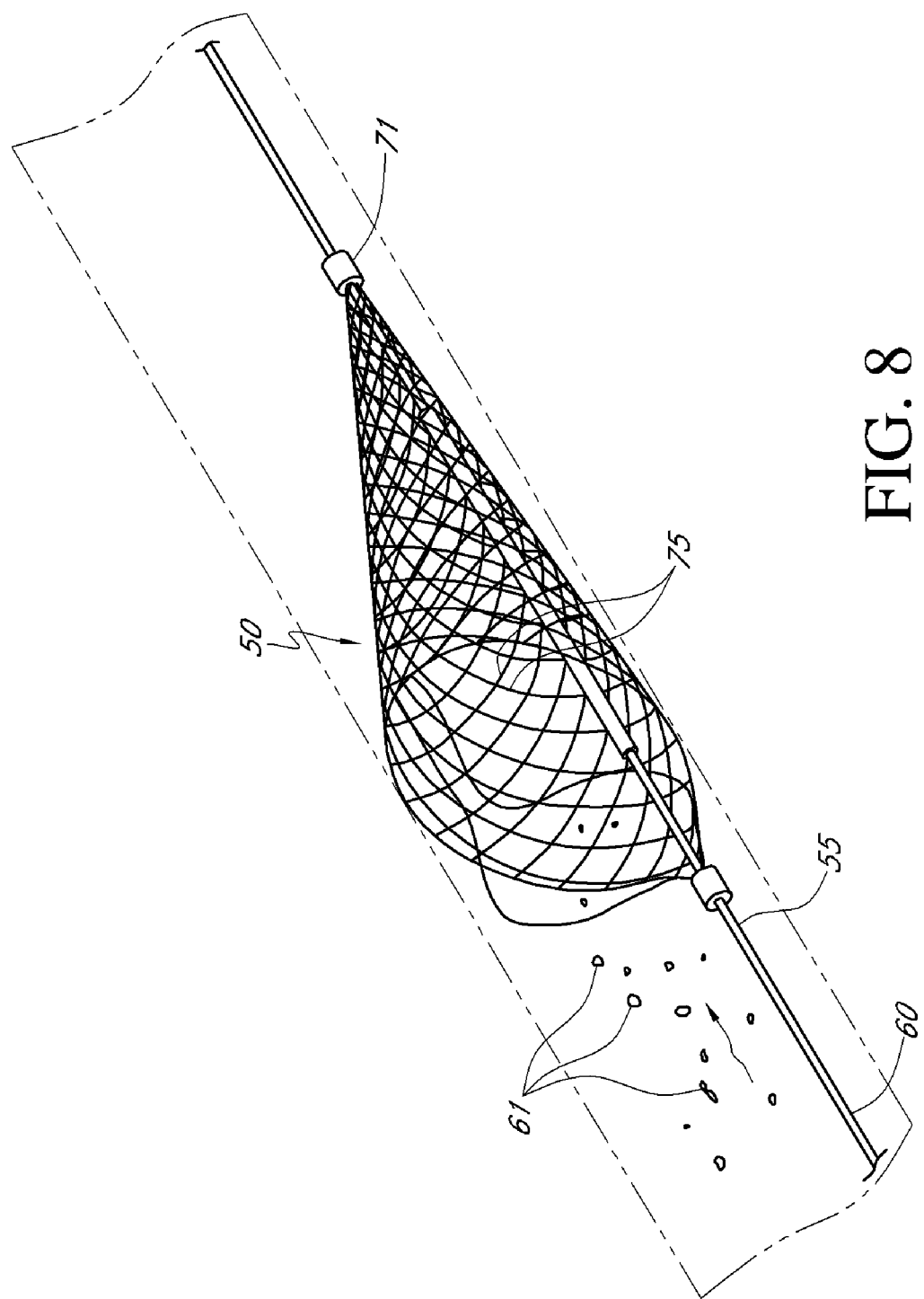
FIG. 8 is a perspective view of a lumen deployed filter.

In some embodiments, embolic protection devices are formed using amorphous metal elements. Embolic protection devices formed of amorphous metal elements can be distal protection devices or proximal protection devices and can be filtering devices or occlusive devices. The filtering, occlusive, or partially occlusive portion of the device may be comprised of woven filaments, knitted filaments, braided filaments, nonwoven filaments processed into a cotton ball like structure, perforated sheet, or other filtering, occlusive, or partially occlusive portion forms. As a first embolic protection device example, amorphous metal filaments can be formed and then braided to form an embolic protection device. FIG. 8 shows a filter similar to the vascular filter disclosed in U.S. Patent Pub. No. 2002/0188314, incorporated by reference ("'188314 filter").

Referring to FIG. 8, the vascular filter 50 is coupled to a distal region 55 of a guide wire 60. The filter 50 has a retracted configuration while inside a catheter sheath (not shown), and an expanded configuration as shown for capturing emboli and particulate matter 61. Proximal and distal sliders 70, 71 are slidable along the guide wire independently of one another as disclosed in U.S. Pat. No. 6,843,798, incorporated by reference, such that the distance between the proximal slider 70 and the distal slider 71 can be varied to effect different configurations of the filter 50. In some embodiments, a stop may be positioned on the guide wire between the proximal slider 70 and the distal slider 71 to bias the distal slider 71 during distal travel of the filter 50 and to bias the proximal slider 70 during proximal travel of the filter, thereby axially elongating the filter 50 when the filter is moved. The stop and slider combination also provides limited axial travel and unimpeded rotational travel of the guidewire relative to the filter. This allows for axial or rotational motion of the wire during use in the body without commensurate axial or rotational motion of the filter, which could potentially generate emboli that cannot be captured by the filter. The proximal slider 70, distal slider 71 and/or stop may be radiopaque for better fluoroscopic visualization of the position of the filter.

Referring again to FIG. 8, the vascular filter 50 is formed of braided strands 75 of amorphous metal wire or filament. In one example, the '188314 filter was disclosed to be formed of filaments each having a diameter of about 0.001 to 0.010 inches. In contrast, without the crystalline grain structure and crystalline defects in the filament, the filter 50 including amorphous filaments, according to certain embodiments, can be formed of significantly thinner filaments, such as filaments having a diameter of about 0.0005 inches or less (i.e., a filament having a cross-sectional area on the order of $2 \times 10^{-7}$ in$^2$ or less). It is contemplated that filament diameters of between about 0.00050 inches (0.013 mm) and about 0.0050 inches (0.13 mm) are desirable. In various embodiments, filament diameters of about 0.00075 inches (0.019 mm), 0.0010 inches (0.025 mm), 0.0015 inches (0.038 mm), 0.0020 inches (0.051 mm), 0.0030 inches (0.076 mm), or 0.0040 inches (0.10 mm), or ranges between any of the foregoing, are desirable. With a thinner amorphous metal filament, the filter can have a lesser unexpanded diameter, and thus can cross tighter lesions, be deployed in more situations, and be delivered to more tortuous lumen locations due to increased flexibility of the smaller diameter wire. The diameter of the filter (in one example, a maximum diameter of 4 mm), the size of the proximally oriented opening (in one example, 0.5-4 mm) and the size of the pores (in one example, 20-1500 microns) are retained as in the '188314 filter, and thus prove equally effective in trapping and retaining particulate material filtered out of a body fluid. However, the filter may be made to varying dimensions and specifications depending on the application or lumen size.

In another embodiment, a filter 50 is made from amorphous metal filaments having the same diameter filters known in the art. For example, the filter may have the same dimensions as the '188314 filter. In this example, the higher elastic yield limit of the amorphous metal filter has less tendency to yield limit and become deformed or damaged during delivery, use, and recovery in a patient than similar filters made of crystalline metal filaments. In this example, the filter will also have more wall apposition force and consequently a better ability to contact the wall of the lumen in which the filter is deployed, thereby providing a higher degree of assurance that emboli or particulate will not bypass the opening of the filter, particularly for filters deployed in tortuous or bend locations. It is contemplated that filament diameters of between 0.001 inches and 0.010" are desirable. In various embodiments, filament diameters of 0.0015", 0.002", 0.003", 0.004", 0.005", or 0.0065" are desirable.

In one embodiment, an embolic protection filter comprised of amorphous metal filaments has a pore size (the diameter of a circle having the same area as a mesh opening bounded by a perimeter of filaments) ranging from about 10 to about 1,000 microns. In another embodiment, an embolic protection filter comprised of amorphous metal filaments has a pore size of about 20 to about 500 microns. In another embodiment, an embolic protection filter comprised of amorphous metal filaments has a pore size of about 30 to about 250 microns. In another embodiment, an embolic protection filter comprised of amorphous metal filaments has a pore size of about 40 to about 150 microns. In another embodiment, an embolic protection filter comprised of amorphous metal filaments has a pore size of about 50 to about 100 microns.

Figure 9:
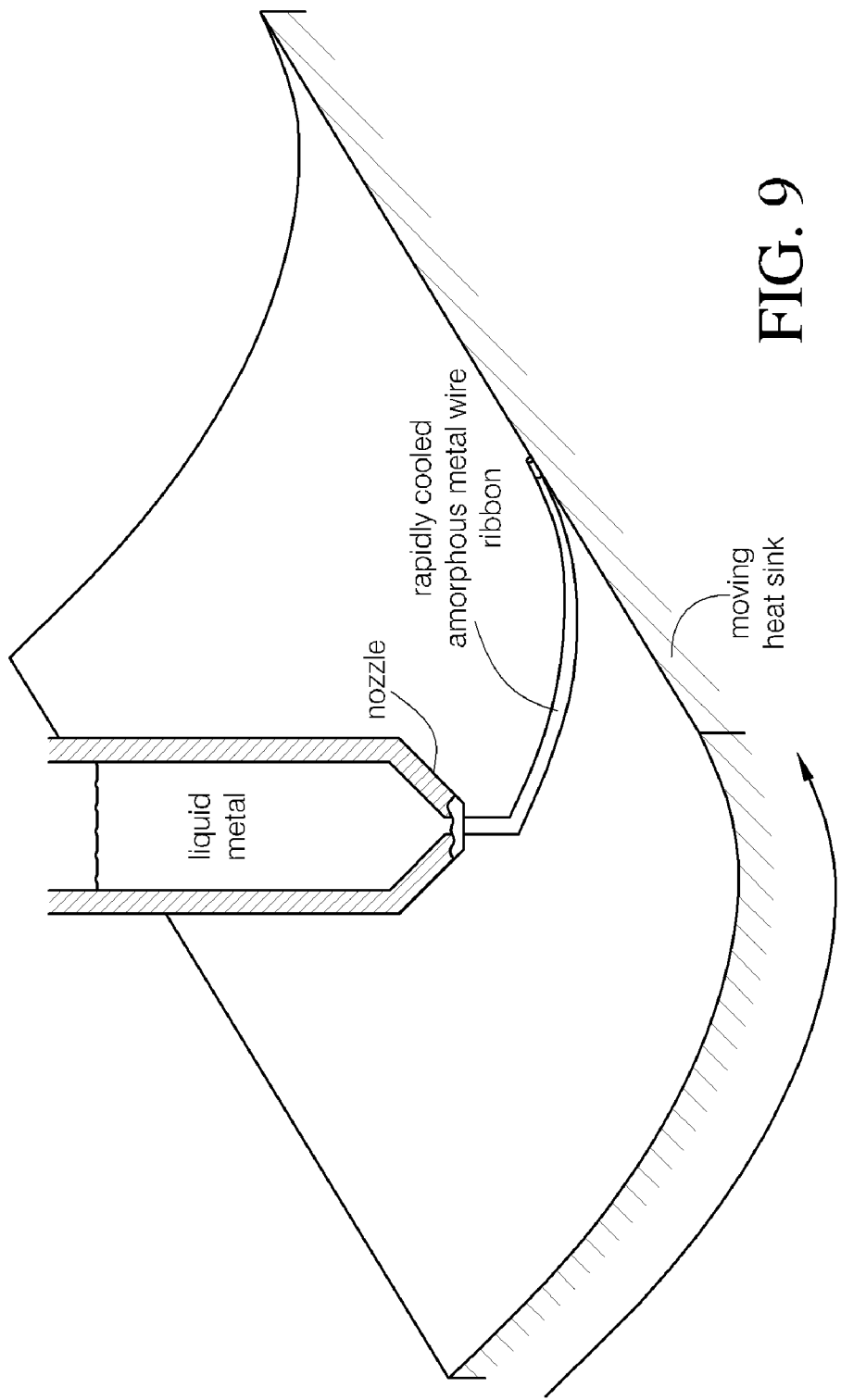
FIG. 9 is a perspective view in partial cross-section of a method of making an amorphous metal wire for use in the filter of FIG. 8.

In one embodiment, to form the thin strands for use in making the vascular filter, a stream of molten metal of a desired metal or alloy composition is sprayed through a nozzle onto a heat sink moving with a velocity relative to the nozzle, as shown in the simplified view of FIG. 9. As one example, the moving heat sink may be a cylinder with the nozzle disposed in the interior of the cylinder to provide a thin stream of molten alloy. With the cylindrical heat sink rotating rapidly about its axis, it quickly removes heat from the thin stream of molten alloy as the nozzle is translated in the direction of the axis of the cylinder to form a solidified wire prior to crystallization of the metal grains. If desired, the nozzle may spray the stream of molten metal through a fluid having a greater convection coefficient than air to further increase heat transfer and cooling rate of the molten metal as it contacts and loses heat to the heat sink on its bottom surface.

In one aspect, when the amorphous metal wire is rapidly cooled on a heat sink to retain the amorphous characteristics of the metal and minimize crystal formation in the metal, the metal wire is not circular in cross-section but rather obtains an aspect ratio and may be considered an amorphous metal wire ribbon. For instance, the amorphous metal wire ribbon shown in FIG. 9 has an aspect ratio with a width which is at least twice its thickness, and more preferably about 5 times its thickness. By providing the wire as a ribbon rather than having a cylindrical cross-section, the resulting wire ribbon bends more easily in directions normal to its thickness than in directions normal to its width. At the same time, the amorphous metal characteristically provides a higher effective strength to the wire ribbon without having crystal defects which rupture under tension or fatigue. Thus, the overall cross-sectional area of the amorphous metal wire can be significantly less than the cross-sectional area of conventional wires used in prior art lumenal devices. For instance, the amorphous metal wire ribbon of the present invention can have a width approximately equal to the diameter of conventional wires used in prior art lumenal devices, but a thickness which is on the order of $\frac{1}{5}^{th}$ the diameter of the conventional wires. Such a filter can have a lower crossing profile yet a similar or improved emboli filtering ability, enabling the filter to cross tighter lesions and to navigate smaller vessels, thus treating more potential patients than prior art filters.

In another aspect, after the amorphous metal wire ribbon is formed, it is further processed such as by wire drawing or swaging to convert the wire closer to a 1:1 aspect ratio such as closer to a square cross-section or, more preferably, to form a wire filament with a circular or near-circular cross-section. By changing the shape of the amorphous metal filament by further processing to a circular cross-section, the amorphous metal filament has no preferential bending direction, making the filter easier to construct and more reliable to self-expand. Thus in one embodiment, a method involves forming amorphous metal wire ribbon, further processing the ribbon to change the cross-sectional aspect ratio, and then using the further processed amorphous metal strand in an internally deployed medical device.

Once the amorphous metal wire or filament is formed, it can be bent and worked at cool temperatures to shape the wire as desired without causing crystallization within the wire. For instance, to form the shape of the filter of FIG. 8, the wire is woven into a braid, with some strands helically wrapped in one direction (e.g., clockwise) and the other strands helically wrapped in the opposite direction (e.g., counterclockwise). A forming mandrel (not shown) is then passed between the wire strands of the braid and positioned within the tubular braid. The forming mandrel has an external molding surface which generally coincides with the desired shape of the filter body. The braid may be drawn down against the forming mandrel by applying axial tension to the braid. The forming mandrel can include a proximal projection having a periphery the size and shape of the desired proximal opening, forcing the wire strands to project about the periphery of the projection. Bands are affixed to both ends of the tensioned and formed wire braid to fix the length of the filaments between bands, thereby causing the amorphous metal braid to retain a shape similar to that of the forming mandrel.

In some embodiments, the amorphous metal wire can also be heat set at a temperature or time which is insufficient to induce significant crystallization, or at a time and temperature sufficient to cause partial or even complete crystallization. After rapid cooling of the molten metal or alloy to form the solid metal wire, the wire is formed under stress about a molding surface (typically a mandrel) into a desired "remembered" shape.

Figure 10:
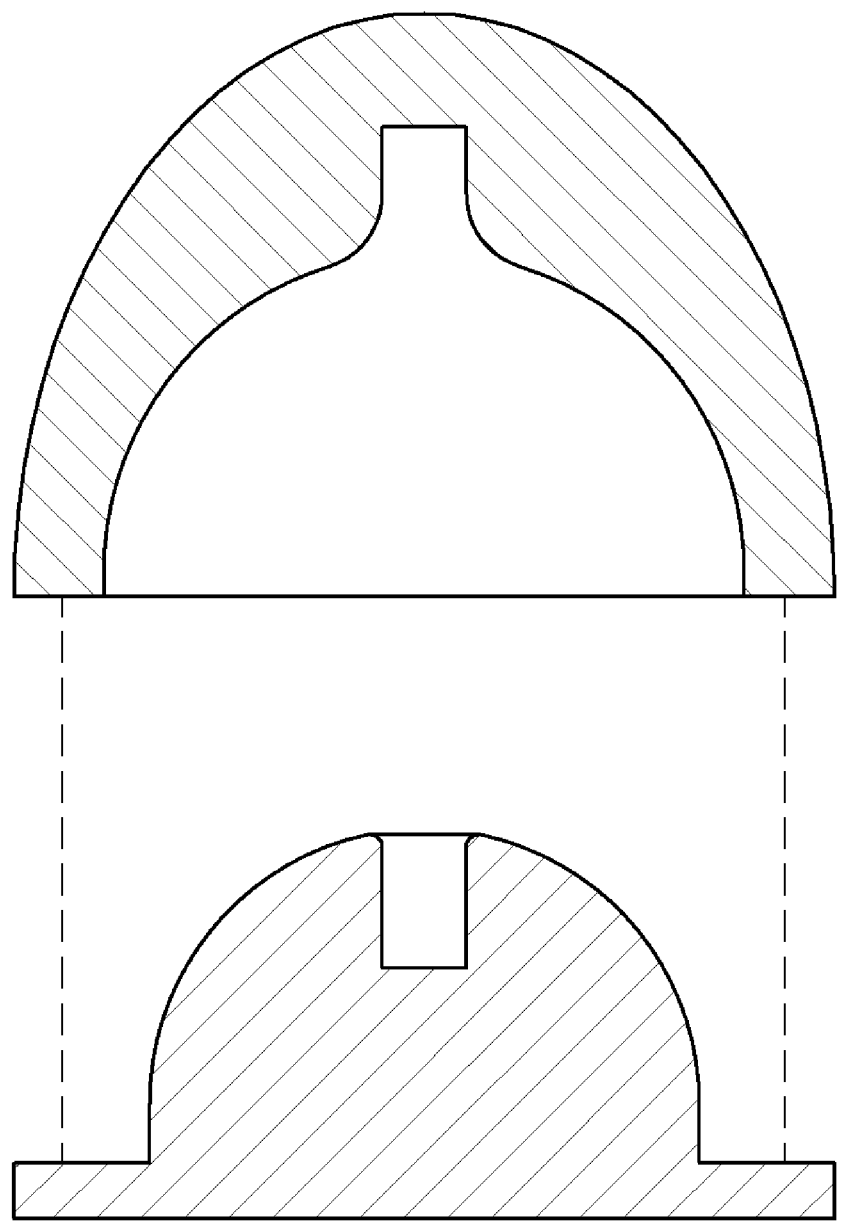
FIG. 10 is a cross-sectional view of a mold used for shape setting wires formed of amorphous metal.

Alternatively or in conjunction to applying stress to the wire during a shape forming stage, a two-sided mold as shown in FIG. 10 may be used to press the wire from both sides into the desired shape. According to one embodiment, the wire is heat set in that shape by heating the wire to a temperature less than the glass transition temperature ($T_g$) of the metal or alloy). Following the predetermined heat treatment, the wires then retain a suitable amount of the deformation induced by the molding surface without significant crystallization of the amorphous metal. In another embodiment, the wire is heat set in that shape by heating the wire to a temperature near to or above the glass transition temperature ($T_g$) of the alloy. Following this predetermined heat treatment, the wires then retain a suitable amount of the deformation induced by the molding surface with at least partial crystallization of the metal. In a filter produced by the above methods, the wires can be elastically collapsed into a lumen of a catheter for delivery to the desired luminal site in the body, and when released from the catheter reassume the desired heat set shape.

As an alternative to conventional molds and mandrels, after the wire is formed under stress about a molding surface into a desired shape, the wire can be held in place with a heat resistant solidifying substance such as plaster of paris, concrete, ceramic, paint and/or glue as disclosed in WO 01/101118, incorporated by reference. The solidifying substance allows filter wires or filaments to be restrained during the shape setting heat treatment and is subsequently removed prior to use of the filter in a patient.

D. Other Amorphous Metal Medical Devices

FIGS. 11-23 show alternative embodiments of wire filter structures manufactured and deployed in accordance with certain embodiments. All of these filters can be comprised of amorphous metal strands and the resultant mesh can have the advantages described above in connection with FIG. 8. For example, in various embodiments all of the filters of FIGS. 11-23 can have one or more of reduced profiles due to reduced wire cross sectional areas, similar profiles but higher wall apposition strengths, and can be shape set, when comprised of amorphous metal filaments instead of crystalline metal filaments.

The wire filter structure of FIGS. 11A and 11B is similar to that of U.S. Pat. No. 7,048,752, incorporated by reference in its entirety ("'752 filter"). The filter 80 includes an umbrella-shaped basket 90 that can be manipulated from the collapsed position shown in FIG. 11A to the expanded position shown in FIG. 11B. The basket 90 is coupled to a guide wire 95 near the distal end of the guide wire 95. In moving from the collapsed position to the expanded position, the wire fabric 100 of the basket 90 folds in on itself, forming a two-layered cup shaped basket 90 in the expanded position. Tethers 110 extend from a strap 115 affixed on the guide wire to the radial edge 120 of the basket 90. When retraction of the basket 90 is desired for removal of the filter, an external catheter (not shown) can be advanced over the tethers 110 to draw the peripheral edge of the basket 90 radially inward.

Unlike the '752 filter, the filter of FIGS. 11A and 11B is formed of amorphous metal strands and the resultant filter has the advantages described above. While the wires of the '752 filter are disclosed to be between about 0.0020 and about 0.006 inches (about 0.051 and about 0.15 mm) in diameter, the amorphous metal wires according to certain embodiments are about 0.00050 to about 0.010 inches (about 0.013 mm to about 0.25 mm) or less in diameter. In other embodiments, the amorphous metal wires are about 0.002 to about 0.006 inches in diameter. The size of pore openings between wires remains similar to the '752 filter, selected based upon the fluid being filtered, such as openings of about 20 to about 500 microns. In some embodiments, the tethers 110 are advantageously comprised of amorphous metal having superior strength and flexibility as compared to crystalline materials.

Figure 12:
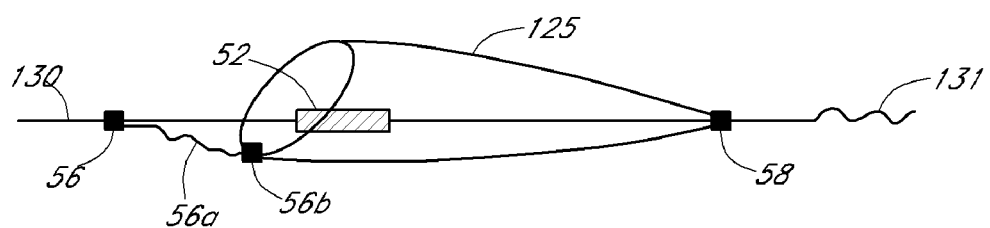
FIG. 12 is a simplified side view of a no loop filter in expanded state.

As shown in FIG. 12, certain embodiments of amorphous metal wire or filaments can be used in an embolic filter similar to that of U.S. Patent. Pub. No. 2004/0153119, incorporated by reference in its entirety ("'153119 filter"). A windsock-shaped filter 125 is coupled to an elongate support member 130 via a distal sliding element 58. A proximal axially fixed element 56 is attached to the elongate support member and is tethered 56*a* to a proximal edge 56*b* of the filter 125. A stop 52 on the elongate support member 130 limits the range of travel of the distal sliding element 58 and the tether 56*a* limits the proximal travel of the elongate member 130 relative to the filter 125. The elongate support member 130 terminates in a floppy tip 131. The resultant filter 125 and tether 56a may have one or more of the advantages of amorphous metal wires or filaments described above.

Figure 13:
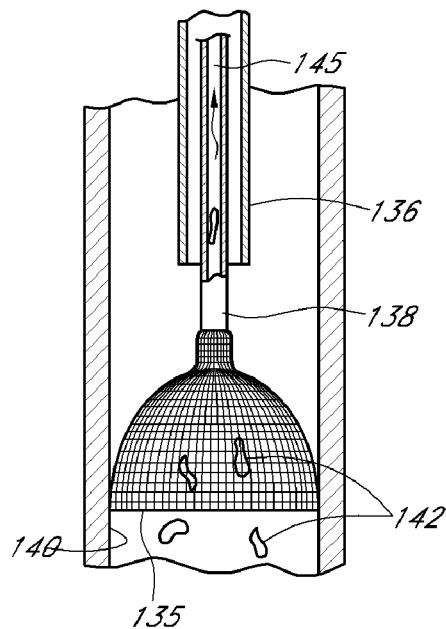
FIG. 13 is a side view, partially in section, of a filter device in its expanded state showing particles being aspirated through the inner catheter into the suction device.

Certain embodiments may also involve amorphous metal wires or filaments used together with a self expanding umbrella or funnel-like filters, similar in design to the vena cava filters of U.S. Pat. No. 5,549,626, incorporated by reference in its entirety ("'626 filter"). FIG. 13 shows a filter 135 in its expanded state by positioning the filter 135 beyond the distal end of an outer catheter 136. The filter 135 is attached to a tube 138 and the tube 138 can be used to provide infusion or aspiration to the vicinity of the filter 135. The expanded diameter of the filter 135 is sufficient to contact the vessel wall 140. As the filter 135 collects emboli and thrombi 142, it may be flushed by applying syringe pressure through the lumen of an inner catheter 145. The '626 filter is formed of crystalline metal filaments such as steel, while the filter as described herein is formed of amorphous metal strands. The resultant filter has one or more of the advantages described above.

Figure 14:
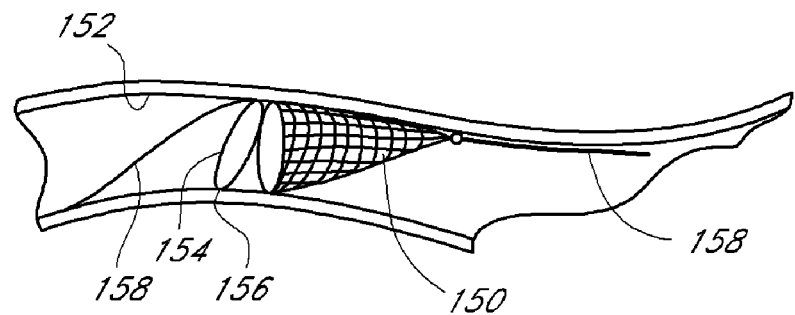
FIG. 14 is a side view of a distal protection device in its deployed state within a curving internal lumen.

Certain embodiments also include distal protection devices including filters positioned with a guide wire but arranged with the basket being to one side of the guide wire, similar to the distal protection device of U.S. Pat. No. 6,740,061, incorporated by reference in its entirety ("'061 distal protection device), or the distal protection device of U.S. Patent Pub. 2004/0153119, incorporated by reference in its entirety ("153119 distal protection device"). FIG. 14 shows a distal protection device with its filter 150 in its expanded state, which is deployed in a curving section of a lumen 152. The distal protection device includes a loop 154 at the proximal end of the filter 150 which opens against the vessel wall 156 of the filter deployment site. The loop 154 is attached to the guide wire 158 to bias the guide wire 158 tighter against the vessel wall 156 even in sections where the vessel is curving or tortuous. With the guide wire 158 positioned closely against the vessel wall 156, the mouth of the filter 150 self-expands to filter 150 the substantial entirety of the cross-section of the vessel flow. The filter 150 is formed of one or more amorphous metal strands. Additionally, in contrast to the crystalline nitinol or steel material for the loop of the '061 distal protection device, the loop 154 may also be formed of one or more amorphous strands, either as a single strand or a multi-stranded cable. The cross-sectional thickness of the wire of the loop 154 is selected based upon the desired elasticity and opening force. In some embodiments, the resultant filter and/or loop made of one or more amorphous metal strands have one or more of the advantages described above.

Figure 15:
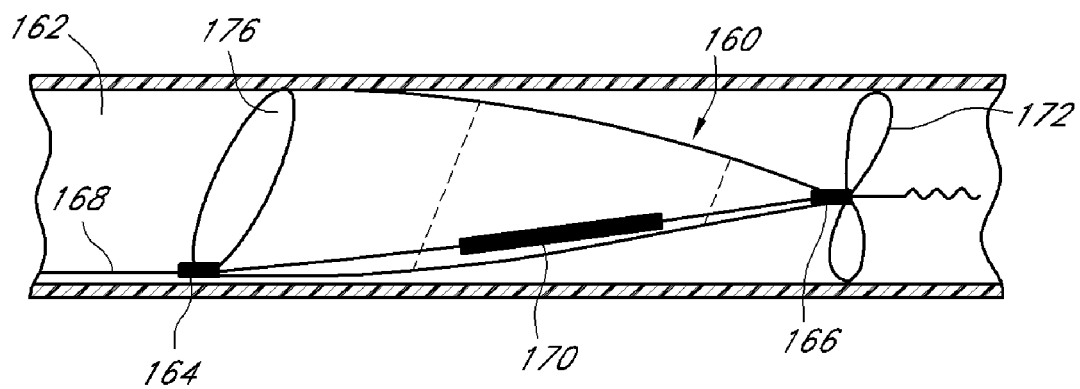
FIG. 15 is a simplified side view of a filter with loop in an expanded, deployed state.

FIG. 15 shows one embodiment of a distal protection device with its filter 160 in its expanded state, which is deployed in a lumen 162 in the patient's body. The filter element 160 is attached between a proximal slider 164 and a distal slider 166, both slidably riding on the guide wire 168 and generally retained at a distal area of the guide wire 168 by a stop 170. The distal protection device includes a loop 172 positioned at the distal end of the filter element 160 which opens against the vessel wall 174 of the filter deployment site. The loop 172 is attached to the filter element 160 and extends on opposing sides of the guide wire 168 to bias the guide wire 168 to a central location relative to the vessel wall 174 and thereby increase the area of the filter 160 unapposed to the vessel wall 174. The filter 160 has a mouth 176 which opens at a proximal end of the filter 160 to filter a substantial entirety of the cross-section of the vessel flow. The filter 160 may be made of one or more amorphous metal strands. In some embodiments, in contrast to the crystalline nitinol or steel material for the distal loop of the '153119 distal protection device, the distal loop 172 can be formed of one or more amorphous metal strands, either as a single strand or a multi-stranded cable. In some embodiments, the cross-sectional thickness of the wire of the loop 172 is selected based upon the desired elasticity and opening force. According to some embodiments, one or more of the resultant filter and loop have one or more advantages of amorphous metals as described above.

Figure 16A:
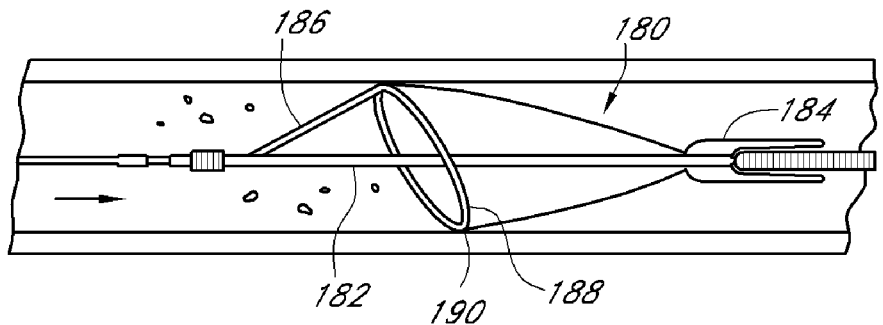
FIG. 16A is a simplified side view of a vascular device deployed in a vessel of a first diameter.
Figure 16B:
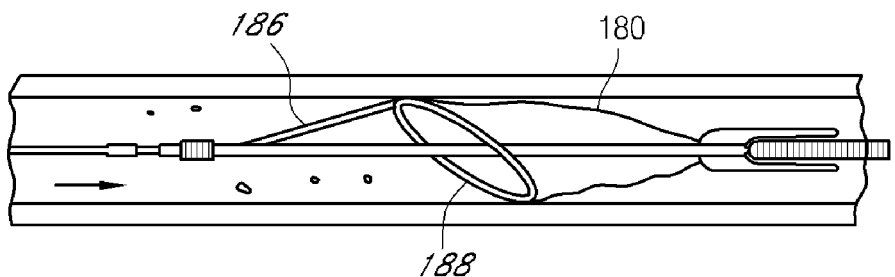
FIG. 16B is a simplified side view of the vascular device of FIG. 16A deployed in a vessel of a smaller diameter.
Figure 16C:
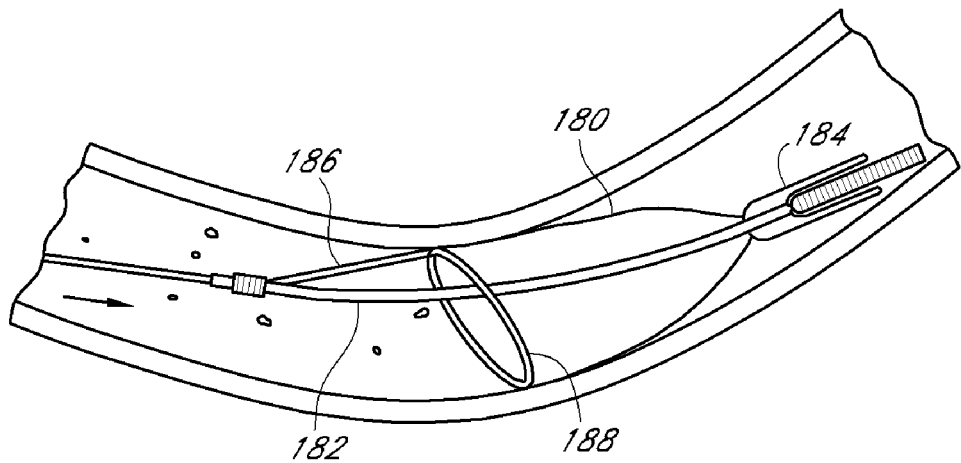
FIG. 16C is a simplified side view of the vascular device of FIGS. 16A and 16B deployed in a curving vessel.

Certain embodiments also include vascular devices having suspension struts and hoops. FIGS. 16A, 16B and 16C show a vascular device similar to that of U.S. Patent Pub. No. 2002/0022858, incorporated by reference in its entirety ("'22858 vascular device"). As shown, the vascular device includes a filter 180, which is coupled to a guide wire 182 at its distal region. The filter 180 has a nose cone 184 and is coupled to the guide wire at its proximal end with a suspension strut 186 and hoop 188. The guidewire 182 passes through the interior of the filter cavity, and lateral motion of the guidewire 182 tends to push the filter 180 and hoop 188 into apposition with a vessel wall 190. The filter 180 may be formed of one or more amorphous metal strands in the form of woven filaments, knitted filaments, braided filaments, non-woven filaments processed into a cotton ball like structure, may be comprised of perforated sheet, or other filtering, occlusive, or partially occlusive forms. In an alternate embodiment, the filter mesh may be comprised of polymer film having holes formed therein using heat generation processes such as laser drilling. The suspension strut and hoop of the '22858 vascular device was disclosed to be a 0.0035 inch nitinol wire, tapered on its ends by grinding, chemical etching or electroless polishing to 0.002 inch point. In contrast to the crystalline nitinol material for the suspension strut and hoop of the '22858 vascular device, the suspension strut 186 and hoop 188 according to embodiments described herein can be formed of one or more amorphous metal strands, either as a single strand or a multi-stranded cable. In some embodiments, the cross-sectional thickness of the wire of the suspension strut 186 and hoop 188 is selected based upon the desired elasticity and opening force. In one embodiment, the amorphous metal wire may be tapered to have a shape similar to the hoop of the '22858, provided that the tapering process does not involve sufficiently increased temperatures or conditions to cause significant crystallization. One or more of the resultant filter, strut or hoop formed at least in part of amorphous metal may have the advantages of amorphous metal described above.

Figure 16D:
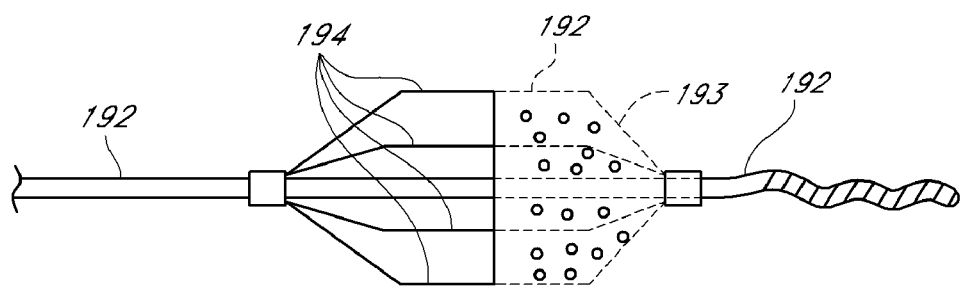
FIG. 16D is a simplified side view of an alternative filter device.

In another embodiment, a filter having struts is shown in FIG. 16D. The filter of FIG. 16D is a vascular device similar to that of U.S. Pat. No. 6,391,044, incorporated by reference in its entirety ("'044 vascular device"). The filter 190 is coupled to the guide wire 192 at its proximal end, slideably coupled to the guidewire 192 at its distal end, and expanded by means of several axial struts 194 to which a filter mesh 193 is attached. The guidewire 192 passes through the interior of the filter cavity. The filter mesh 193 is preferably formed of one or more amorphous metal strands in the form of woven filaments, knitted filaments, braided filaments, non-woven filaments processed into a cotton ball like structure, may be comprised of perforated sheet, or other filtering, occlusive, or partially occlusive forms. The struts 194 are preferably formed of one or more amorphous metal strands, perforated sheet, cut tubing, or other forms. In an alternate embodiment the filter mesh 193 may be comprised of polymer film having holes formed therein using one or more heat producing processes such as laser drilling. In contrast to the crystalline nitinol material for the struts of the '044 vascular device, the struts 194 can be formed partially or completely of amorphous metal, either as a single strand or a multi-stranded cable. In some embodiments, the cross-sectional thickness of the wire of the struts is selected based upon the desired elasticity and opening force. In some embodiments, the resultant amorphous metal filter and/or struts have one or more advantages of amorphous metal materials described above.

Figure 17:
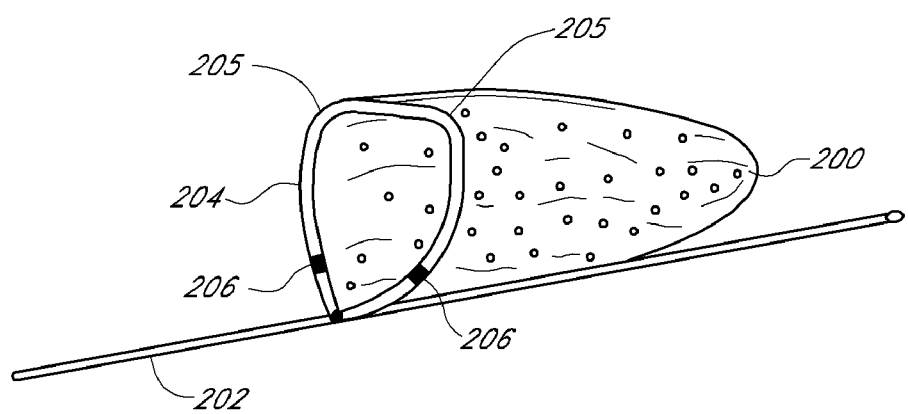
FIG. 17 is a perspective view of a vascular device in a deployed state.

Certain embodiments also include vascular devices having articulation points in a hoop. FIG. 17 shows a vascular device similar to that of U.S. Patent Pub. No. 2003/0100919, incorporated by reference it is entirety ("'100919 vascular device"). The vascular device includes a filter 200, which is attached to a guide wire 202 at its proximal end and supported and held open with a hoop 204. In some embodiments, radiopaque marker bands 206 may be applied to the hoop to aid in fluoroscopic imaging. In some embodiments, the hoop 204 includes one or more articulation regions 205 which provide a point of increased bending of the hoop 204 when the vascular device is collapsed. Said articulation regions may comprise locally thinned regions of hoop 204, softened regions of hoop 204, or points of increased bending produced by other means.

In one embodiment, the hoop 204 is formed of amorphous metal, with the overall cross-sectional thickness selected based upon the desired elasticity of opening force. In some embodiments, the articulation region may have a non-circular cross-section or a reduced thickness. For instance, the cross-sectional shape or dimensions of the articulation region may be modified to provide greater flexibility by drawing, cold working, swaging, grinding, chemical etching or electroless polishing, provided that the reshaping process does not involve sufficiently increased temperatures or conditions to cause significant crystallization.

In a second embodiment, the hoop 204 is initially formed of amorphous metal, with one or more regions which are subsequently heat treated or aged to induce crystallization. With part of the hoop wire 204 being a crystallized metal and part of the hoop wire 204 being amorphous metal, the hoop wire has different stiffness and rigidity characteristics at different positions. One or more articulation regions 205 are formed to be more flexible than the rest of the hoop due to the different amounts of crystallization and amorphous metal along the length of the wire of the hoop 204.

Figure 18:
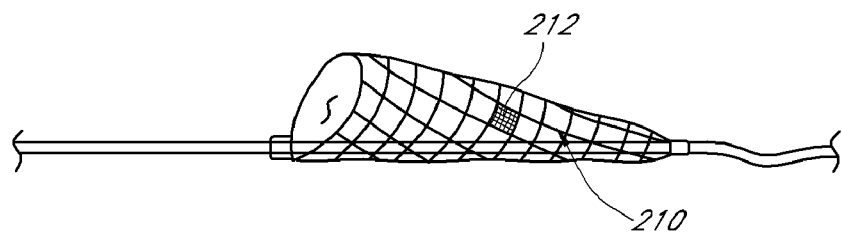
FIG. 18 is a simplified side view of a distal protection device in a deployed state.
Figure 19:
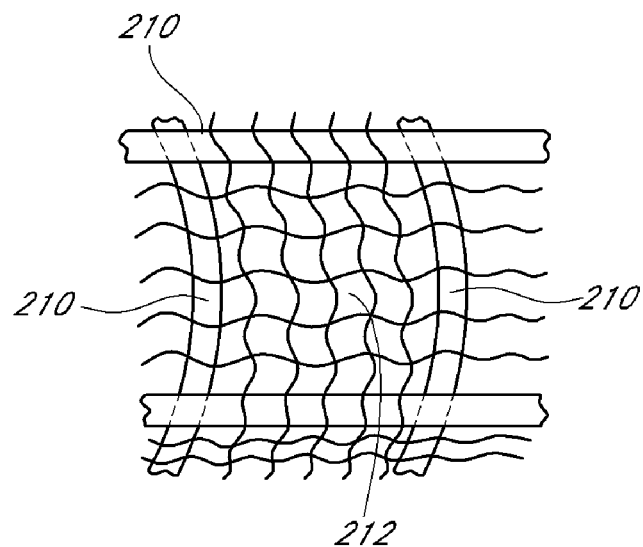
FIG. 19 is an enlarged view of a portion of the distal protection device of FIG. 18, illustrating a section of a wire frame having a fiber matrix secured to the frame.

Certain embodiments include a wire frame 210 for a distal protection device. FIGS. 18 and 19 show a distal protection device similar to that of U.S. Patent. Pub. No. 2002/0128680, incorporated by reference in its entirety ("'128680 distal protection device"). According to one embodiment, the distal protection device includes a filtering material 212 such as an electrospun polymer fiber matrix, which is attached over an expandable and collapsible wire frame 210. While in the figure only one pore in the expandable frame 210 is shown as filled with filtering material 212 it is understood that some or all of the frame 210 may be covered with filtering material 212 over the interior of the frame, the exterior of the frame, in the pores of the frame, or any combination thereof. The wire frame material of the '128680 distal protection device was disclosed to be a 0.0015 to 0.005 inch (0.038 mm to 0.13 mm) wire formed of nylon, polyester, PEEK, polyimide, liquid crystal polymers, Teflon, Tefzel, polyurethanes, shape memory polymers, ELGILOY, MP35N, spring steel, stainless steel, titanium, nitinol or the like. According to embodiments described herein, the wire frame material can be at least partially formed of amorphous metal, either as a single strand or a multi-stranded cable. In some embodiments, the cross-sectional thickness of the wire of the wire frame is selected based upon the desired elasticity and opening force.

Figure 20:
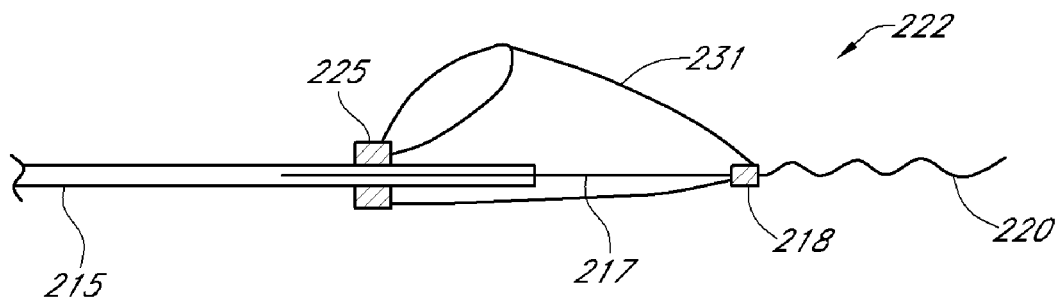
FIG. 20 is a schematic side view of a vascular protection device deployed with a distal elongate support segment telescoped within the lumen of a proximal elongate support segment.
Figure 21:
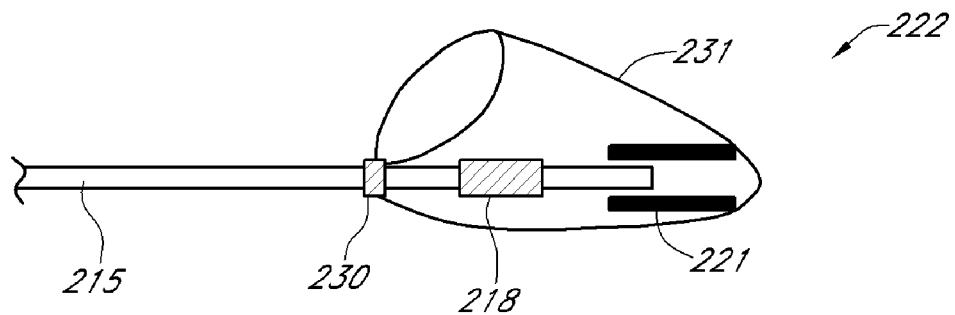
FIG. 21 is a schematic side view of a vascular protection device having a proximal elongate support segment telescoped within the lumen of a distal elongate support segment.

Certain embodiments include vascular protection devices having discontinuous or continuous elongate support members. FIGS. 20 and 21 show distal protection devices similar to those of U.S. Pat. Pub. No. 2003/0171771 incorporated by reference ("'171771 vascular protection devices"). According to certain embodiments described herein, the vascular protection device of FIG. 20 has a proximal elongate support member 215 shaped as a lumen and a wire 217 providing a distal elongate support member 218 which can telescope in and out of the proximal elongate support member 215. In some embodiments, a floppy tip 220 is provided on a distal end of the vascular protection device. In some embodiments, the filter 222 is attached between a proximal fixed element 225 fixed to the proximal elongate support member 215 and one or more distal elements 218 fixed to the elongate support member 215. One or more components of the device may be made at least partially of amorphous metal. For example, the filter mesh 231, elongate support members 215, 218, or other elements, may be formed at least in part of amorphous metal. In some embodiments, the cross-sectional thickness of the elongate support members is selected based upon the desired elasticity and opening force. In some embodiments, one or more of the resultant filter, elongate support members, or other elements have one or more of the advantages described above.

Referring to FIG. 21, the vascular protection device according to some embodiments has a filter attached between a proximal sliding element 230 and a distal sliding element 221. A stop 218 is affixed to the elongate support member 215, positioned to stop sliding of the distal sliding element 221 such that the elongate support member 215 is always contained within the distal sliding element 221. The distal and proximal sliding elements 230, 221 allow the filter to move longitudinally and rotate axially with respect to the elongate support member 215 and about the stop 218. The filter mesh 222 and/or elongate support members 215 according to some embodiments are formed at least in part of amorphous metal. In some embodiments, the cross-sectional thickness of the elongate support members is selected based upon the desired elasticity and opening force. In some embodiments, the resultant filter 226 and elongate support members 215 have the advantages described above.

Figure 22:
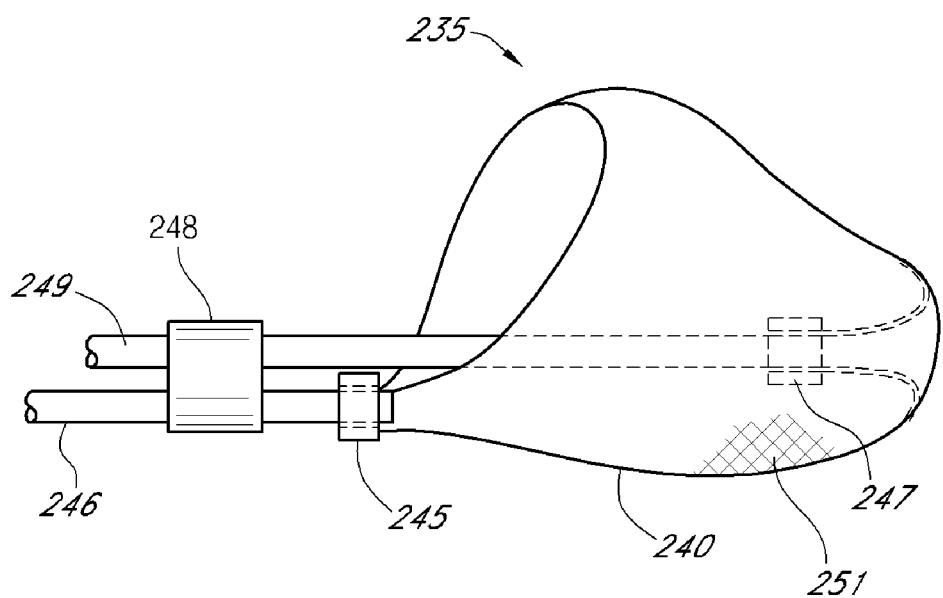
FIG. 22 is a fragmentary, perspective view of an everted filter device.

Certain embodiments also include an everted filter device 235. FIG. 22 shows an everted filter device 235 similar to that of U.S. Patent Pub. No. 2003/0176884, incorporated by reference in its entirety ("'176884 everted filter device"). According to certain embodiments described herein, the everted filter device 235 of FIG. 22 includes a filter member 240 attached between a proximal ring or collar 245 on a proximal shaft 246 and a distal ring or collar 247 on a distal shaft 249. The proximal ring or collar 248 can be fixedly attached to either the proximal shaft 246 or the distal shaft 249, but not both. By changing the longitudinal location of the distal shaft 249 relative to the proximal shaft 246, the extent of eversion of the filter 235 may be controlled. The filter mesh 251 and/or elongate support members 246, 249 may be formed, at least in part, of amorphous metal. In some embodiments, the cross-sectional thickness of the elongate support members is selected based upon the desired elasticity and opening force. In some embodiments, one or more of the resultant filter and elongate support members may have one or more advantages of amorphous metal materials described above.

Figure 23A:
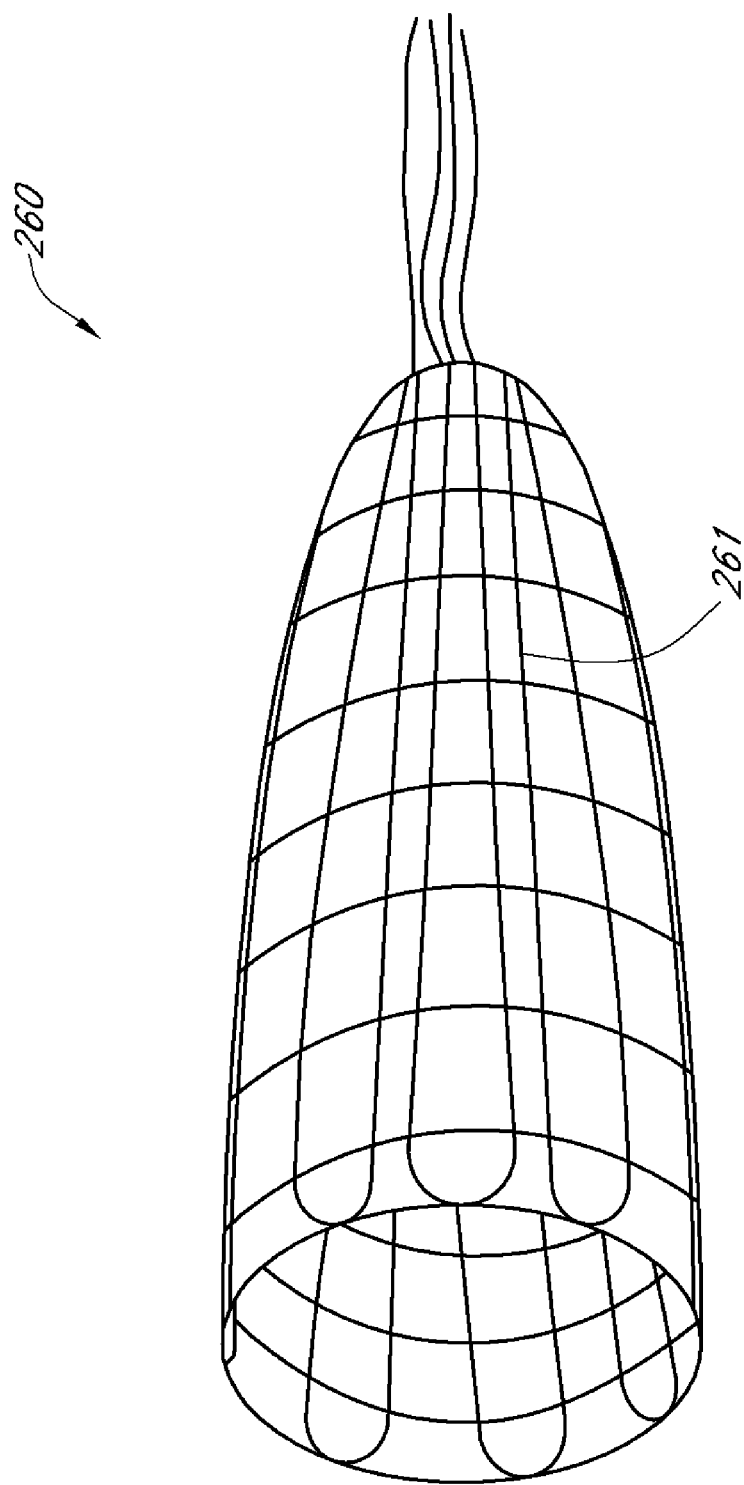
FIG. 23A is a simplified perspective view of a knitted filter.
Figure 23B:
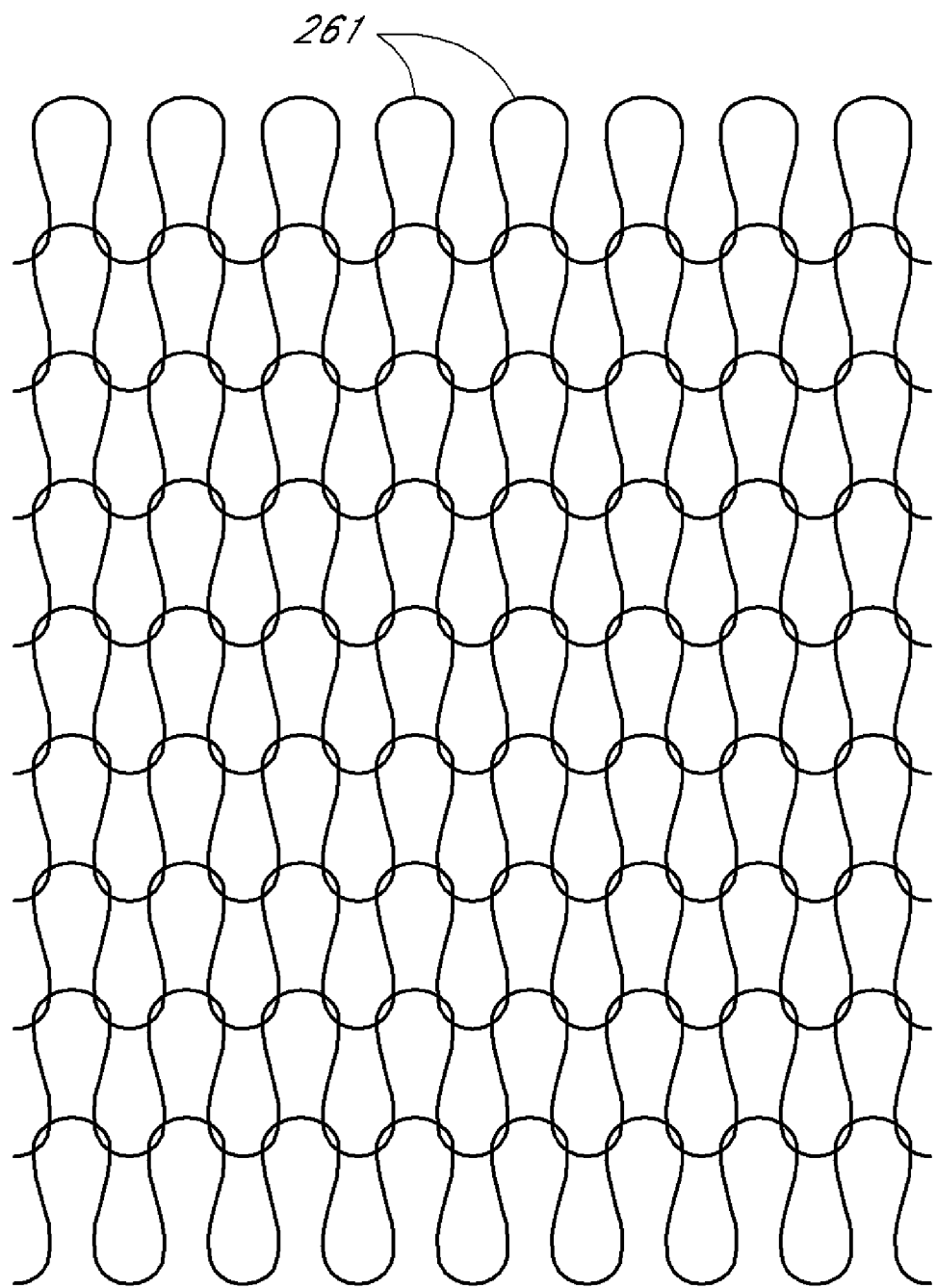
FIG. 23B is an enlarged view of a portion of the knitted filter of FIG. 23A.

Certain embodiments also include knitted filters. FIGS. 23A and 23B depict an embolic filter 260 with its pore size controlled by knitting, similar to that as described in U.S. Patent Pub. No. 2004/0153117, incorporated by reference in its entirety ("'153117 filter"). In some embodiments, the filter 260 can have an overall windsock shape shown in FIG. 23A by circular knitting of wires 261, more closely shown in FIG. 23B. In contrast to the material used to knit the '153117 filter, the material used to knit the filter of FIGS. 23A and 23B may include amorphous metal. The resulting filter mesh is formed at least in part of amorphous metal. In some embodiments, the resultant filter 260 has the advantages described above.

For any of the shaped internally deployed medical devices of FIGS. 8 and 11-23, a mold mandrel can be used to form the desired shape of the amorphous metal structure. The mold or mandrel can be formed of a material that dissolves, vaporizes or can otherwise be removed as disclosed in WO 02/101118, incorporated by reference in its entirety. The small diameter wire mesh provided by the amorphous metal wire, according to certain embodiments, is particularly useful when the mold or mandrel is removed by a process which includes vibrating or otherwise breaking the mold or mandrel. In particular, the smaller diameter wire in some embodiments is useful in wedging into small cracks and crevasses of the mold or mandrel during breaking of the mold or mandrel, facilitating the breakage into small enough pieces that they can fit between the pores of the device.

Coatings may be placed over the amorphous metal wire of these various filter embodiments for various desired performance attributes. For instance, radiopaque coatings, or drug (such as an antibiotic, anticoagulant, or growth hormone) or other active agent release coatings, may be applied over the amorphous metal wire structures. Lubricity may be provided by a coating of a low friction polymer such as polyurethane, hydrogels, polyethylene, polytetrafluoroethene (PTFE) and TEFLON. Polymer films such as silicone, polyurethane, or other materials can be applied to the filter mesh to cause the mesh to become occlusive. Alternatively the mesh can be manufactured with very little open area between adjacent filaments so as to render the mesh functionally occlusive for a given application.

Figure 24:
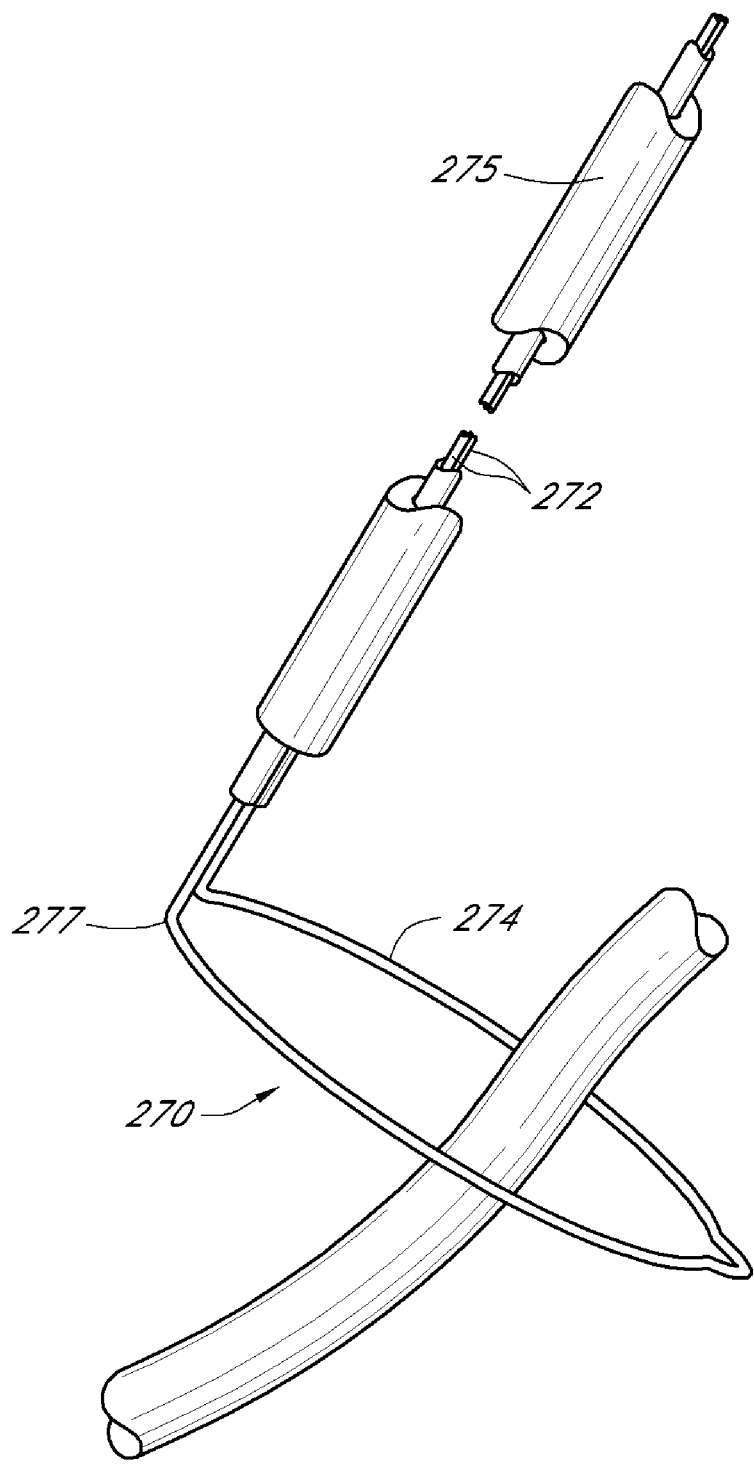
FIG. 24 is a perspective view of a snare device.

Another internally deployed medical device that may be formed at least in part of an amorphous metal is a snare. One example of a snare 270 is shown in FIG. 24, which is similar to the snare disclosed in U.S. Pat. No. 5,171,233, incorporated by reference ("'233 snare"). In some embodiments, the snare 270 includes an elongate proximal member 272 and a loop-shaped distal segment 274 oriented at an angle to the adjacent portion of the proximal member. The snare 270 can be advanced inside a catheter 275 to a region of interest, with the loop-shaped distal segment 277 returning to its angled orientation once extended beyond a distal end of the catheter sheath. In the '233 snare, the wire for the loop-shaped distal segment is disclosed to be formed of nitinol, with a wire diameter between about 0.005 inches and 0.025 inches, or a cable of several strands of a diameter of about 0.003 to 0.004 inches. According to some embodiments described herein, the loop-shaped distal segment 274 of the snare 270 can also include either a monofilament or multi-stranded cable, but is made of one or more wires of either circular or ribbon-like cross-section of amorphous metal. Additionally, the proximal member 272 can be formed of amorphous metal wire, to provide superior strength with flexibility to the entire snare structure. The amorphous metal wires may be formed as disclosed above in connection with other wire structures.

Figure 25:
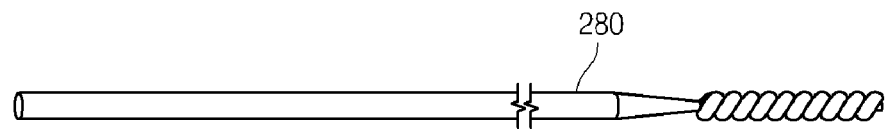
FIG. 25 is a side view of a guide wire.
Figure 26:
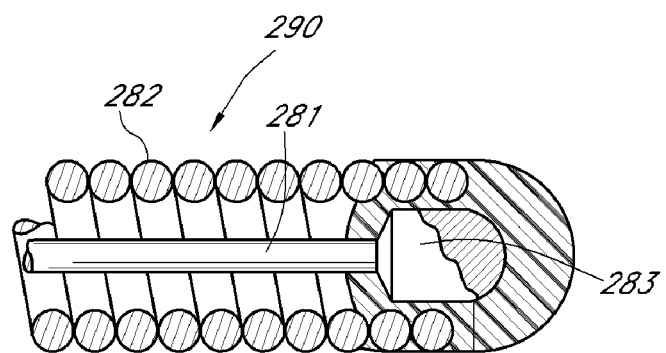
FIG. 26 is a side cross-sectional view of a distal end of the guide wire of FIG. 25 having a coil.

FIGS. 25-28 show embodiments of guide wires using amorphous metal components. FIG. 25 shows an overall view of an exemplary guide wire 280, and FIG. 26 shows an enlarged view of the distal tip 290 of the guide wire 280 similar to the guide wire of U.S. Pat. No. 5,067,489, incorporated by reference ("'489 guide wire"). In some embodiments, the guide wire includes a distally tapered central core 281 and a coil 282 helically wrapped about the central core 281 with some spacing between the core and the coil. In some embodiments, a plug 281 is provided at a distal end of the guide wire 280. In the '489 guide wire, the wire coil is a single helix formed of stainless steel. In contrast, the wire coil 282 according to certain embodiments described herein is formed at least in part of amorphous metal. The wire of the coil 281 may be provided as either a monofilament or multi-stranded cable, made of one or more wires of either circular or ribbon-like cross-section of amorphous metal. The amorphous metal wires may be formed as disclosed above in connection with other wire structures. In some embodiments, the plug 283 is adhered to the coil 282 with an epoxy or with a polymeric resin which sets at a temperature low enough to not cause significant conversion of the amorphous metal into crystalline structure. Prior art coils are known to fracture in the body during use. According to some embodiments, the amorphous metal coil provides advantages of superior strength with flexibility to a guidewire.

In addition to forming the wire coil of amorphous metal, the core 281 of the guide wire 280 can be formed at least in part of amorphous metal. An amorphous metal core 281 for the guide wire 280 is particularly advantageous for small diameter guide wires such as those used in neurovascular surgery. Crystalline metal cores are known to break, especially in the small diameter neurovascular guide wires. In some embodiments, a substantial amount of the strength of the distal tip 290 comes from the core 281 rather than the outer coil 282. As such, embodiments that provide an amorphous metal core 281 adds strength and flexibility to the guide wire 280, making the core 281 less likely to break in tension, compression or fatigue as the guide wire 280 is traversed through a tortuous path.

Figure 27:
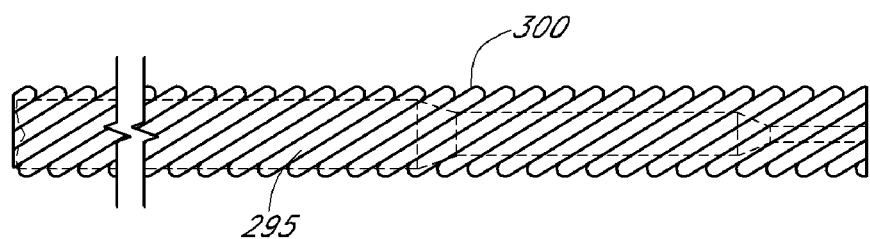
FIG. 27 is a side view of a guide wire having multiple helically wrapped wire strands.

FIG. 27 shows an alternative distal tip of the guide wire similar to the guide wire of U.S. Patent Pub. No. 2005/0027212, incorporate by reference ("'27212 guide wire"). The guide wire includes a central core 295 and a plurality of wire 300 strands helically wrapped about the central core 295 with some spacing. In the '27212 guide wire, the wire strands are a multiple helix formed of titanium and its alloys, cobalt-chromium-nickel-molybdenum-iron alloy (ELGILOY), stainless steel, tungsten, platinum, or engineered polymers such as liquid crystal polymers, polyetheretherketone (PEEK), polyimide, and polyester, having diameters ranging from 0.0025 cm (0.001 inch) to about 0.025 cm (0.010 inch). According to certain embodiments as described herein, the wire strands 300 are at least partially formed of amorphous metal. In some embodiments, the wire strands 300 may be provided as either a monofilament or multi-stranded cable, each made of one or more wire filaments of either circular or ribbon-like cross-section of amorphous metal. According to certain embodiments, the amorphous metal wire strands 300 may be formed as disclosed above in connection with other wire structures. A polymer tie layer (not shown) may be applied over the amorphous metal strands 300, provided that the polymer tie layer is attached at low temperature, so as to not induce crystal grain formation in the amorphous strands, using methods such as casting, thermomolding, extrusion, fusing, bonding, sintering, or other methods known in the art. For instance, the polymer tie layer may be formed of polyfluorotetraethylene (PTFE) or other fluorinated polymers, parylene, polyurethanes, or silicones. Prior art coils are known to fracture in the body during use. According to certain embodiments, the amorphous metal coil provides advantages of superior strength with flexibility, or other has other advantages as described herein.

Figure 28A:
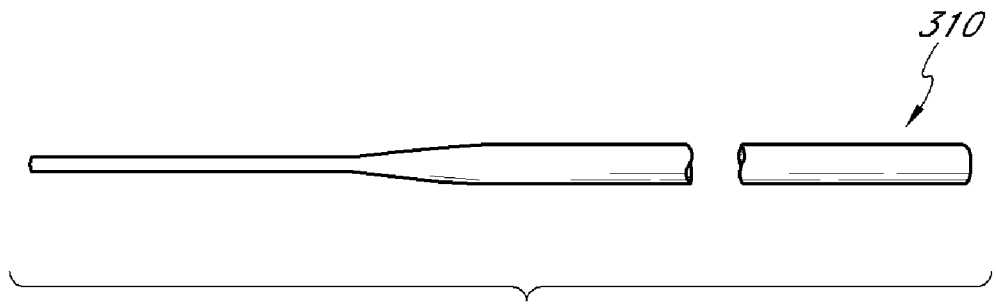
FIG. 28A is a side view of a metal core for a guide wire.
Figure 28B:
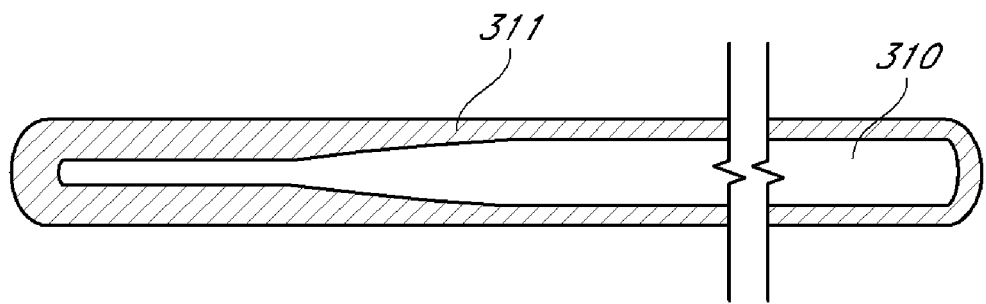
FIG. 28B is a side view in partial cross-section of the core of FIG. 28B with a polymeric coating.

FIGS. 28A and 28B show a monofilament guidewire 310, which may have a polymeric coating. FIG. 28A shows a section of a central core of a guide wire similar to the guide wire of U.S. Pat. No. 4,925,445, incorporate by reference in its entirety ("'445 guide wire"). The core of the '445 guide wire is disclosed to be formed of a super-elastic alloy such as a titanium-nickel alloy, a copper-zinc alloy, or a nickel aluminum alloy, having a diameter in the range of 0.05 to 1.5 mm. In contrast, the core according to embodiments of as described herein is formed of amorphous metal. In some embodiments, the core may be provided as either a monofilament or multi-stranded cable, each made of one or more wires of either circular or ribbon-like cross-section of amorphous metal. In some embodiments, the amorphous metal wire may be formed as disclosed above in connection with other wire structures. Prior art cores are known to fracture in the body during use. According to some embodiments, the amorphous metal core provides advantages of superior strength with flexibility.

FIG. 28B shows the guide wire 310 in a polymeric coating 311. According to certain embodiments, a polymeric coating may be used on amorphous metal parts of medical devices. In the example as shown in FIG. 28B, the polymeric coating 311 is attached at low temperature, so as to not induce crystal grain formation in the amorphous metal core, using methods such as casting, thermomolding, extrusion, fusing, bonding, sintering, or other methods known in the art. For instance, the polymeric coating 311 may be formed of one or more of polyfluorotetraethylene (PTFE) or other fluorinated polymers, parylene, polyurethanes, polyethylene, TEFLON, or silicones.

Figure 29:
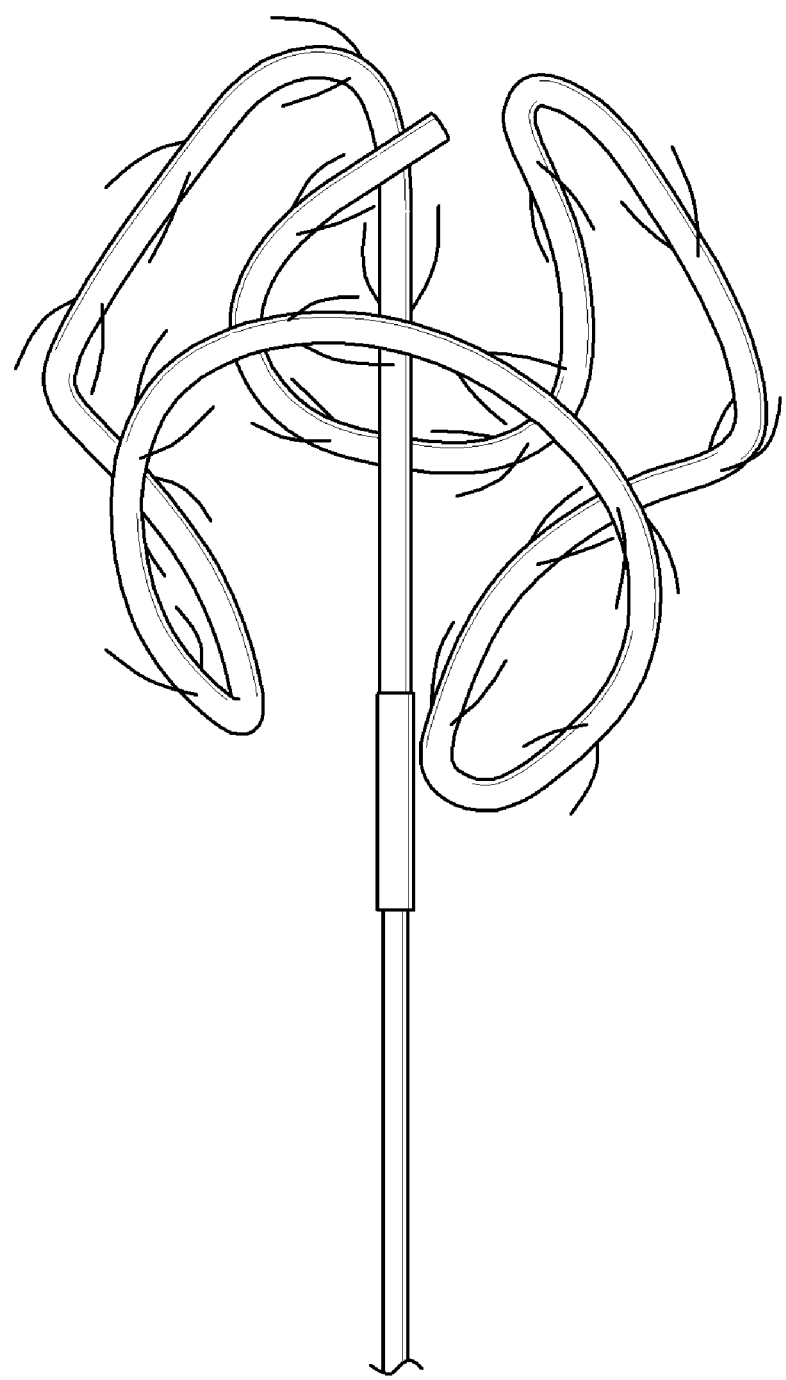
FIG. 29 is a perspective view of a neurologic coil.

Certain embodiments include medical device coils. For example, FIG. 29 shows a neurologic coil similar to an ATLAS 3-D embolic detachable coil marketed by ev3, Inc. of Plymouth, Minn. Rather than formed of nitinol, the embolic coil may be formed at least in part of amorphous metal. In some embodiments, a coil, such as an embolic coil, may be provided as either a monofilament or multi-stranded cable, each made of one or more wires of either circular or ribbon-like cross-section of amorphous metal. In some embodiments, amorphous metal wires may be formed as disclosed above in connection with other wire structures. In certain embodiments, the amorphous metal embolic coils invention provides advantages of superior strength with flexibility, or other advantages as described herein.

The internally deployed medical devices formed at least in part of amorphous metal can also take other forms. For instance, amorphous metal structures can be used as either the stylet or as reinforcing elements in balloon catheters, delivery catheters, recovery catheters, guide catheters, diagnostic catheters, aspiration catheters, and other catheters as are known in the art. Amorphous metal structures can be used in treatment devices for aneurysms and arteriovenous malformations ("AVMs") as well as other neurovascular disorders of the brain and spinal cord. In particular, such neurological systems can use amorphous metal coils and coil delivery systems in ways similar to those discussed above for stents. In ways analogous to the stent embodiments disclosed above, amorphous metal structures can be used in closure devices for patent foramen ovale ("PFOs") and left atrial appendages ("LAAs") or in treating other defects such as patent ductus arteriosus, atrial septal defects ("ASDs"), and ventricular septal defects ("VSDs").

The particular metal or alloy which is used in any of the amorphous metal structures depends upon the intended use and desired functions of the medical device. In certain embodiments, the amorphous metal is chosen for its biocompatibility in the intended application. In some embodiments, the amorphous metal is a bulk solidifying amorphous alloy. For instance, the amorphous metal can be stainless steel, alloys of nickel and titanium similar to nitinol, alloys of zirconium and/or titanium, ELGILOY, HASTELLOY, INCOLOY, alloys of cobalt and chromium, bioabsorbable metals such as magnesium alloys, radiopaque materials such as gold or platinum, etc. Certain amorphous metals may be an alloy including one or more metals selected from zirconium, titanium, nickel, copper, iron, beryllium, aluminum, silicon, niobium, copper, nickel. Other transition metals may also be included in some embodiments. One can alternatively select other alloys that cannot be easily processed in crystalline form. In some embodiments, the metal/alloy is solidified at a sufficiently fast rate and under conditions such that the formation of a crystalline or granular structure in the solid form of the metal/alloy is inhibited. Radiopaque crystalline materials may be also used in combination with the amorphous metal, or the amorphous metal may be coated with radiopaque markings, as desired for the intended imaging of the internally deployed medical device.

Certain embodiments involve methods of using amorphous metal devices. For example, a medical device comprised of amorphous metals may be used at a luminal site in the body of a patient. Using known medical techniques, a diseased or damaged portion of a patient's blood vessel may be identified. Using techniques well known in the art, a guide wire, such as the nonlimiting guide wire examples shown in FIGS. 25-28, is percutaneously inserted into the patient's blood vessel and advanced to the luminal region of interest.

In some embodiments, an embolic protection device or an embolic protection delivery catheter is advanced to the region of interest over the guidewire, the guidewire is withdrawn, and the embolic protection device is deployed. In an alternate embodiment the embolic protection device is deployed before the guidewire is withdrawn. For instance, a distal filter or a proximal occlusive device may be deployed downstream or upstream respectively of the treatment site, positioned such that the body of the filter is in a healthy region of vessel suitable for use as a landing zone for the filter or device or such that the proximal occlusive device is upstream of the treatment site. The embolic protection device may comprise filters such as those shown in FIGS. 8 and 11-23. In some embodiments, the embolic protection delivery catheter (if used) is withdrawn from the vicinity of the filter. In some embodiments, the operator can use fluoroscopy or other methods to ascertain that the mouth of the filter is adequately deployed against the vessel wall with no gaps, downstream to the region of interest, and upstream to any important side branch vessels. In some embodiments, the operator can use fluoroscopy or other methods to ascertain that the occlusive device is adequately deployed against the vessel wall with no gaps, upstream to the region of interest.

If desired, pre-dilatation of the region of interest may be performed in advance of treatment using known angioplasty catheters. A stent, such as one of the stents shown in FIGS. 1-3 and 5-7, may be chosen with the correct length and diameter for the vessel or lumen being treated. In one embodiment, a stent delivery system such as depicted in FIGS. 6 and 7 is advanced over the guidewire to the region of interest. Using imaging techniques such as fluoroscopy, the ends of the stent are positioned at a location relative to the region of interest. In some embodiments, radiopaque contrast media may be injected at this time or at any time to assist with visualization of the patient's anatomy and/or the stent. In one embodiment, the inner member of the stent delivery system is held stationary and the sheath is proximally retracted to expose the stent. As the sheath is withdrawn, the stent expands into contact with a lumenal wall of the vessel. If desired, radiopaque markers may be imaged before, during and/or after stent deployment for evaluating the position of the stent relative to the treatment site, evaluating the extent of diametrical expansion of the stent, and for other reasons. In some embodiments, the stent delivery system is withdrawn and removed from the patient's body.

Once the vessel has been treated, the embolic protection device is withdrawn from the vessel. For example, in the case of a distal filter, a catheter is advanced to the region of interest and over the filter to substantially close the opening(s) of the filter, and the filter together with any captured particles is removed from the patient's body.

If a stent becomes loose from a stent delivery system, or if a device such as a catheter or guidewire fractures, leaving a foreign article in the body, a snare such as that shown in FIG. 24 may be used to recover the foreign article from the lumenal system. To recover the foreign article, a guidewire is advanced into the body and past the foreign article. A snare loop is passed over the proximal end of the guidewire and the snare is drawn into a snare catheter leaving a bit of the snare loop extending out of the distal end of the snare catheter. In one embodiment, the snare/snare catheter assembly is advanced over the guidewire into the patient's body until the snare loop is in the vicinity of the foreign article. The snare loop may be advanced out of the end of the snare catheter and manipulated until the snare loop encircles the foreign article. Then the snare catheter is advanced while holding the snare loop stationary until the snare loop cinches around the foreign article. Then the snare and snare catheter are held in fixed axial relation to each other while they are withdrawn from the body, carrying the foreign article out of the body as the snare and snare catheter are withdrawn.

In a follow-up visit the patient's treatment site may be imaged using MRI. Use of amorphous metal implants can assure that this can be done safely and without excessive artifact on the MRI images.

Although the present invention has been described with reference to preferred embodiments, workers skilled in the art will recognize that changes may be made in form and detail without departing from the spirit and scope of the invention. As one example, while deployment of the present invention is described with reference to use in a lumen such as a blood vessel (vein or artery) having a defined flow direction, it is envisioned that the invention can be applied to other conduits in the body as well including bronchi, ducts, ureters, urethra, and other lumens, and to other treatment locations which are accessed through such lumens.

What is claimed is:

1. A medical device comprising an amorphous metal, wherein the medical device is a shape set medical device, the shape set medical device comprising between about 0.5 volume percent to about 75 volume percent crystalline portions formed from shape setting the medical device to partially convert amorphous metal into crystalline metal to impart crystalline properties to the medical device.

2. The medical device of claim 1, wherein the medical device is a stent.

3. The medical device of claim 2, wherein the stent is self expanding.

4. The medical device of claim 2, wherein the stent is balloon expandable.

5. The medical device of claim 1, wherein the medical device comprises one or more amorphous metal filaments having a diameter between about 0.010 inches (0.25 mm) and about 0.00050 inches (0.013 mm).

6. The medical device of claim 1, wherein the medical device further comprises a coating on at least a portion of the amorphous metal.

7. The medical device of claim 6, wherein the coating comprises one or more of a radiopaque coating, a drug coating, an active agent release coating, a biocompatible coating, or a lubricious coating.

8. The medical device of claim 1, wherein the medical device is sufficiently corrosion resistant to be internally biocompatible.

9. The medical device of claim 1, wherein the medical device is capable of imaging under MRI.

10. The medical device of claim 1, comprising between about 5 volume percent to about 75 volume percent crystalline metal.

11. A medical device comprising amorphous metal portions and crystalline metal portions, wherein the crystalline metal portions have a structure formed by shape setting an amorphous metal to convert said amorphous metal into partially crystalline metal, wherein between about 0.5 volume percent to about 75 volume percent of the amorphous metal is converted to crystalline metal.

12. The medical device of claim 11, wherein the medical device is a filter.

13. The medical device of claim 12, wherein the filter is a braided filter.

14. The medical device of claim 11, wherein the medical device is a stent.

15. The medical device of claim 14, wherein the stent is self expanding.

16. The medical device of claim 14, wherein the stent is balloon expandable.

17. A medical device comprising an at least partially amorphous metal surface, wherein the at least partially amorphous metal surface has improved corrosion resistance when the at least partially amorphous metal surface is compared to a more crystalline metal surface, wherein the medical device is a stent, the at least partially amorphous metal surface comprising crystalline portions formed by shape setting at least a portion of the medical device, the crystalline portions comprising between about 0.5 volume percent to about 75 volume percent of the surface.

18. A medical device comprising a structure comprising amorphous metal, wherein the structure has one or more of improved MRI safety or improved MRI compatibility when compared to a more crystalline metal structure, wherein the medical device is a stent, the amorphous metal comprising crystalline portions formed by shape setting at least a portion of the medical device, the crystalline portions comprising between about 0.5 volume percent to about 75 volume percent of the structure.

19. A medical device comprising an amorphous metal structure, wherein the medical device is coated with one or more selected from the group consisting of a radiopaque coating and a lubricious coating, the amorphous metal structure comprising crystalline portions formed by shape setting at least a portion of the medical device, the crystalline portions comprising between about 0.5 volume percent to about 75 volume percent of the structure.

20. The medical device of claim 19, wherein the medical device is a stent.

21. The medical device of claim 1, wherein the shape set medical device comprises crystalline portions having a structure formed by annealing amorphous metal, the shape of the structure substantially maintained upon annealing.

22. The medical device of claim 1, wherein the shape set medical device is configured to maintain a desired shape upon annealing.

23. The medical device of claim 1, wherein the shape set medical device comprises crystalline portions having a structure formed by annealing amorphous metal in a desired shape of the medical device with an elastic yield limit value that is less than an otherwise identical medical device that is not shape set.

24. The medical device of claim 1, wherein the medical device is shape set to lower the elastic yield limit of said medical device.

25. The medical device of claim 1, wherein the shape set medical device comprises an annealed structure.

26. The medical device of claim 1, wherein the shape set medical device comprises an expanded structure.

27. The medical device of claim 1, wherein the crystalline portions are formed from shape setting the medical device to partially convert solidified amorphous metal to crystalline metal.

28. The medical device of claim 10, comprising between about 15 volume percent to about 40 volume percent crystalline metal.

29. The medical device of claim 11, wherein the crystalline metal portions are formed by shape setting a solidified amorphous metal to convert the solidified amorphous metal to partially crystalline metal.

30. The medical device of claim 11, wherein between about 5 volume percent to about 75 volume percent of the amorphous metal is converted to crystalline metal.

31. The medical device of claim 30, wherein between about 15 volume percent to about 40 volume percent of the amorphous metal is converted to crystalline metal.

32. The medical device of claim 17, wherein the crystalline portions comprise between about 5 volume percent to about 75 volume percent of the surface.

33. The medical device of claim 32, wherein the crystalline portions comprise between about 15 volume percent to about 40 volume percent of the surface.

34. The medical device of claim 18, wherein the crystalline portions comprise between about 5 volume percent to about 75 volume percent of the structure.

35. The medical device of claim 34, wherein the crystalline portions comprise between about 15 volume percent to about 40 volume percent of the structure.

36. The medical device of claim 19, wherein the crystalline portions comprise between about 5 volume percent to about 75 volume percent of the structure.

37. The medical device of claim 36, wherein the crystalline portions comprise between about 15 volume percent to about 40 volume percent of the structure.

38. The medical device of claim 1, wherein the medical device is a filter.

39. The medical device of claim 38, wherein the filter is a braided filter.

40. The medical device of claim 1, wherein the medical device is a stent delivery system.

41. The medical device of claim 1, wherein the medical device is a guidewire.

42. The medical device of claim 1, wherein the medical device is a snare.

43. The medical device of claim 1, wherein the medical device is a coil.

44. The medical device of claim 1, wherein the medical device is a catheter.

45. The medical device of claim 1, wherein the medical device is a septal defect closure device.

46. The medical device of claim 1, wherein the medical device is a left atrial appendage closure device.

47. The medical device of claim 1, wherein the medical device is a staple.

48. The medical device of claim 1, wherein the medical device is a clip.

49. The medical device of claim 11, wherein the medical device is a stent delivery system.

50. The medical device of claim 11, wherein the medical device is a guidewire.

51. The medical device of claim 11, wherein the medical device is a snare.

52. The medical device of claim 11, wherein the medical device is a coil.

53. The medical device of claim 11, wherein the medical device is a catheter.

54. The medical device of claim 11, wherein the medical device is a septal defect closure device.

55. The medical device of claim 11, wherein the medical device is a left atrial appendage closure device.

56. The medical device of claim 11, wherein the medical device is a staple.

57. The medical device of claim 11, wherein the medical device is a clip.

58. The medical device of claim 38, wherein the filter is an embolic protection filter.

59. The medical device of claim 38, wherein the filter comprises a wire frame, at least a portion of the wire frame comprising an amorphous metal.

60. The medical device of claim 38, wherein the filter comprises a filter element comprising amorphous metal filaments.

61. The medical device of claim 60, wherein the filter element is braided.

62. The medical device of claim 60, wherein the filter has a pore size ranging from about 10 to about 1000 microns.

63. The medical device of claim 60, wherein the filter has a pore size ranging from about 20 to about 500 microns.

64. The medical device of claim 60, wherein the filter has a pore size ranging from about 30 to about 250 microns.

65. The medical device of claim 60, wherein the filter has a pore size ranging from about 40 to about 150 microns.

66. The medical device of claim 60, wherein the filter has a pore size ranging from about 50 to about 100 microns.

67. The medical device of claim 40, wherein the stent delivery system includes a stylet formed from an amorphous metal.

68. The medical device of claim 40, wherein the stent delivery system includes a reinforcing element formed from an amorphous metal.

69. The medical device of claim 40, wherein the stent delivery system is an over the wire system.

70. The medical device of claim 40, wherein the stent delivery system is a rapid exchange system.

71. The medical device of claim 40, wherein the stent delivery system is a fixed wire system.

72. The medical device of claim 40, wherein the stent delivery system comprises a self expanding stent or a balloon expandable stent.

73. The medical device of claim 72, wherein the self expanding stent or the balloon expandable stent comprises amorphous metal.

74. The medical device of claim 72, wherein the self expanding stent or the balloon expandable stent comprises a shape set amorphous metal.

75. The medical device of claim 41, wherein the guidewire is monofilament, wherein the monofilament comprises amorphous metal.

76. The medical device of claim 41, wherein the guidewire is multi-stranded, wherein one or more of a strand or filament of the multi-stranded guidewire comprises amorphous metal.

* * * * *